United States Patent
Won et al.

(10) Patent No.: US 11,198,733 B2
(45) Date of Patent: Dec. 14, 2021

(54) PHARMACEUTICAL COMPOSITION FOR INHIBITING METASTASIS OF CANCER, COMPRISING, AS ACTIVE INGREDIENT, ANTIBODY THAT SPECIFICALLY BINDS TO EPIDERMAL GROWTH FACTOR RECEPTOR

(71) Applicants: GREEN CROSS CORPORATION, Yongin-si (KR); MOGAM INSTITUTE FOR BIOMEDICAL RESEARCH, Yongin-si (KR)

(72) Inventors: Jong-hwa Won, Yongin-si (KR); Yangmi Lim, Yongin-si (KR); Min-Kyu Hur, Yongin-si (KR)

(73) Assignees: GREEN CROSS CORPORATION, Yongin-si (KR); MOGAM INSTITUTE FOR BIOMEDICAL RESEARCH, Yongin-si (KR)

( * ) Notice: Subject to any disclaimer, the term of this patent is extended or adjusted under 35 U.S.C. 154(b) by 97 days.

(21) Appl. No.: 16/096,988

(22) PCT Filed: Apr. 27, 2016

(86) PCT No.: PCT/KR2016/004418
§ 371 (c)(1),
(2) Date: Oct. 26, 2018

(87) PCT Pub. No.: WO2017/188472
PCT Pub. Date: Nov. 2, 2017

(65) Prior Publication Data
US 2019/0119388 A1    Apr. 25, 2019

(51) Int. Cl.
| | |
|---|---|
| A61K 39/395 | (2006.01) |
| A61P 35/04 | (2006.01) |
| C07K 16/28 | (2006.01) |
| C07K 16/30 | (2006.01) |
| A61K 39/00 | (2006.01) |

(52) U.S. Cl.
CPC ........ *C07K 16/2863* (2013.01); *A61K 39/395* (2013.01); *A61P 35/04* (2018.01); *C07K 16/3046* (2013.01); *A61K 2039/505* (2013.01)

(58) Field of Classification Search
CPC . C07K 16/2863; C07K 16/3046; A61P 35/04; A61K 39/395
USPC .................................................... 424/174.1
See application file for complete search history.

(56) References Cited

U.S. PATENT DOCUMENTS

| | | | |
|---|---|---|---|
| 8,748,175 B2 | 6/2014 | Kim et al. | |
| 2008/0131373 A1 | 6/2008 | Cao | |
| 2012/0231021 A1* | 9/2012 | Kim | A61P 35/00 424/174.1 |
| 2013/0266579 A1 | 10/2013 | Wei et al. | |
| 2013/0309233 A1 | 11/2013 | Zhou et al. | |
| 2016/0068609 A1* | 3/2016 | Goletz | C07K 16/2863 424/133.1 |

FOREIGN PATENT DOCUMENTS

| | | |
|---|---|---|
| JP | 2013505736 A | 2/2013 |
| JP | 2015518872 A | 7/2015 |
| KR | 10-2013-0083090 A | 7/2013 |
| KR | 10-2014-0130749 A | 11/2014 |
| KR | 10-2015-0144804 A | 12/2015 |

OTHER PUBLICATIONS

International Search Report for PCT/KR2016/004418 dated Jan. 26, 2017.
Y. Lim et al: "GC1118, an Anti-EGFR Antibody with a Distinct Binding Epitope and Superior Inhibitory Activity against High-Affinity EGFR Ligands", Molecular Cancer Therapeutics, vol. 15, No. 2, Feb. 1, 2016, pp. 251-263 (14 pages total).
Park Ji Eun et al: "Abstract 3496: GC1118, a novel anti-EGFR antibody, shows more potent antitumor activity regardless of KRAS mutation or high-affinity lignad stimulation compared with cetuximab in gastric cancer", Cancer Research, vol. 78, No. 13, Jul. 2018 (3 pages total).
Do-Youn Oh et al: "A First-in-Human Phase I Study of GC1118, a Novel Anti-Epidermal Growth Factor Receptor Antibody, in Patients with Advanced Solid Tumors", The Oncologist, vol. 24, No. 8, 2019, (16 pages total).
Gerdes, C., et al., "GA201(RG7160): A Novel, Humanized, Glycoengineered Anti-EGFR Antibody with Enhanced ADCC and Superior in Vivo Efficacy Compared with Cetuximab", Clinical Cancer Research, vol. 19, No. 5, 2013, pp. 2-15/E (14 pages).
Arena, S., et al., "MM-151 overcomes acquired resistance to cetuximab and panitumumab in colorectal cancers harboring EGFR extracellular domain mutations", Science Translation Medicine, 2016, vol. 8, No. 324, 324ra14, pp. 2-12/E (11 pages).
Ishida et al., "Trastuzumab-Based Photoimmunotherapy Integrated with Viral HER2 Transduction Inhibits Peritoneally Disseminated HER2-Negative Cancer", Molecular Cancer Therapeutics, vol. 15, No. 3, Mar. 2016, pp. 402-411.

\* cited by examiner

*Primary Examiner* — Yan Xiao
(74) *Attorney, Agent, or Firm* — Sughrue Mion, PLLC

(57) ABSTRACT

The present invention provides a pharmaceutical composition for inhibiting the metastasis of cancer, comprising, as an active ingredient, an antibody that specifically binds to an epidermal growth factor receptor, and a method for inhibiting the metastasis of cancer using the composition. The composition or the method is effective in inhibiting the invasion of various gastric cancer cell lines induced by EGFR ligands. Therefore, the pharmaceutical composition can be usefully used for inhibiting the metastasis of cancer.

5 Claims, 20 Drawing Sheets

Specification includes a Sequence Listing.

[Fig.1]
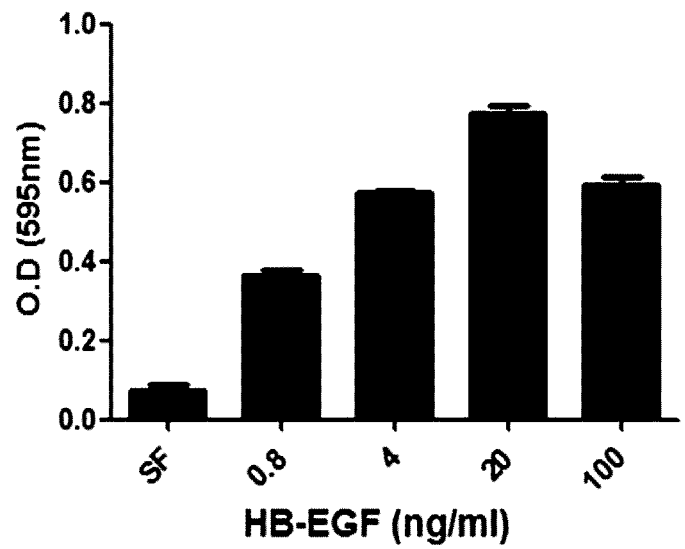
[Fig. 2]
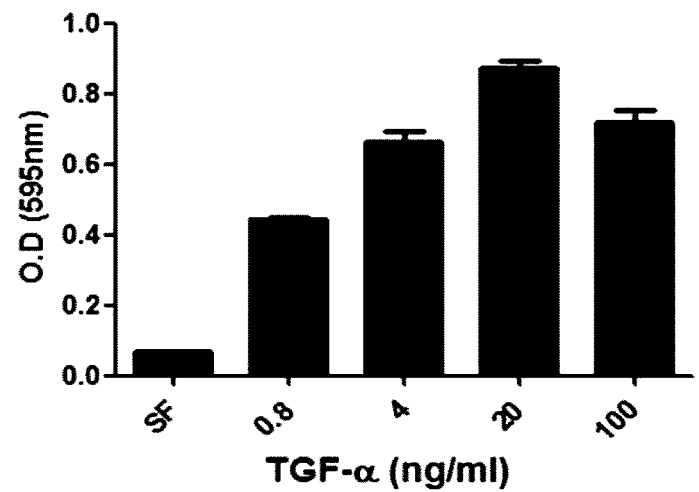

[Fig. 3]
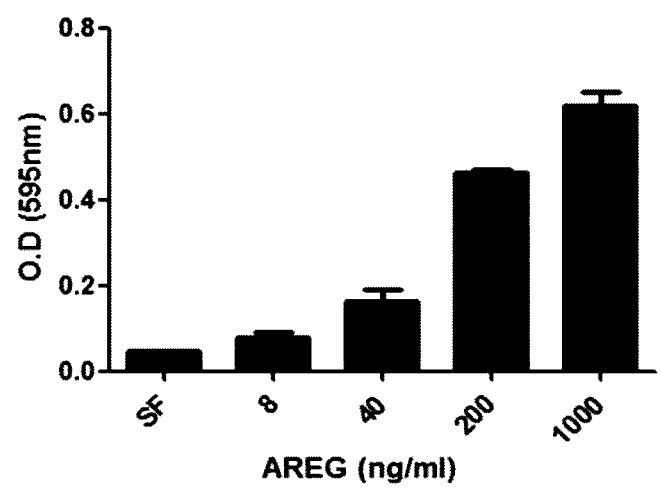

[Fig. 4]
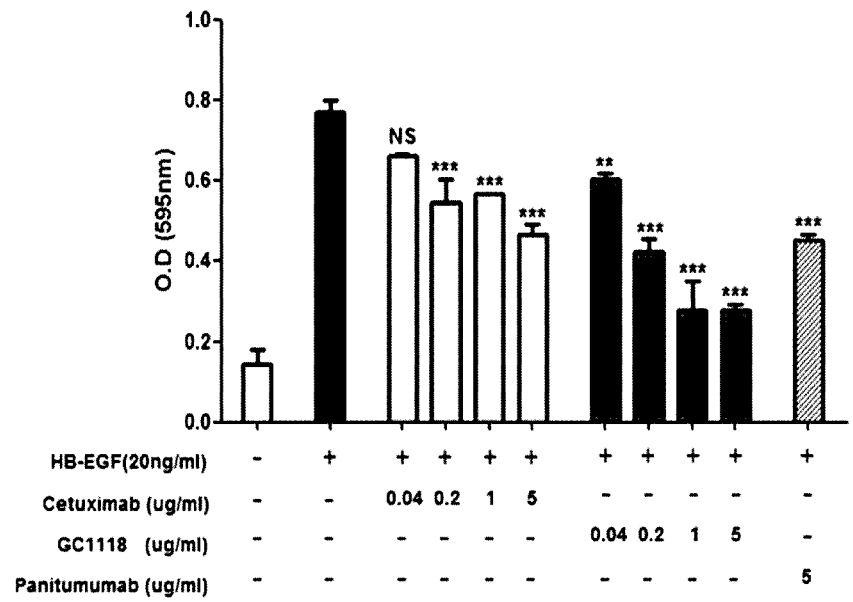
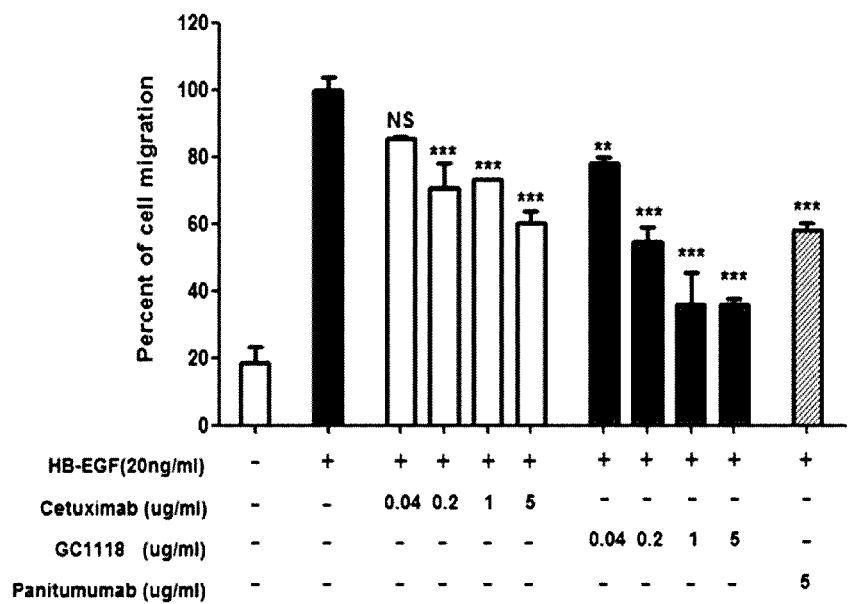

[Fig. 5]
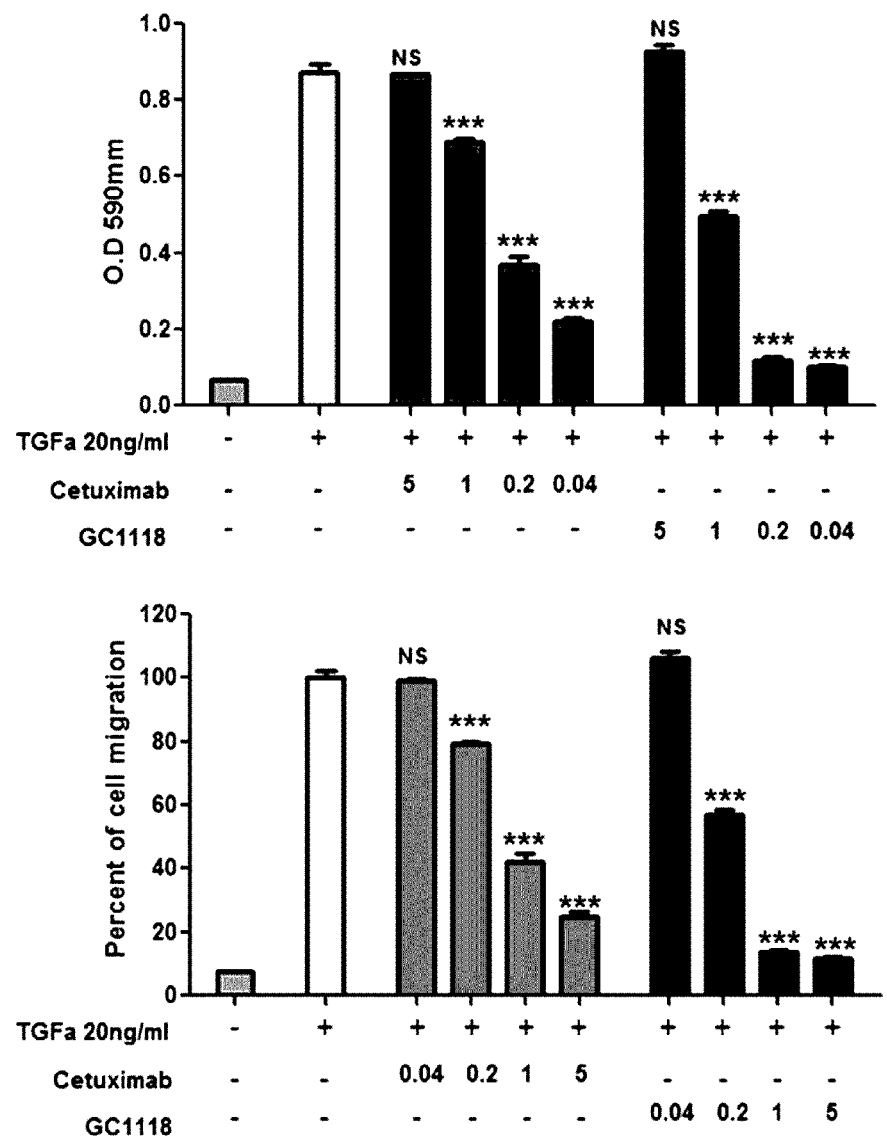

[Fig. 6]
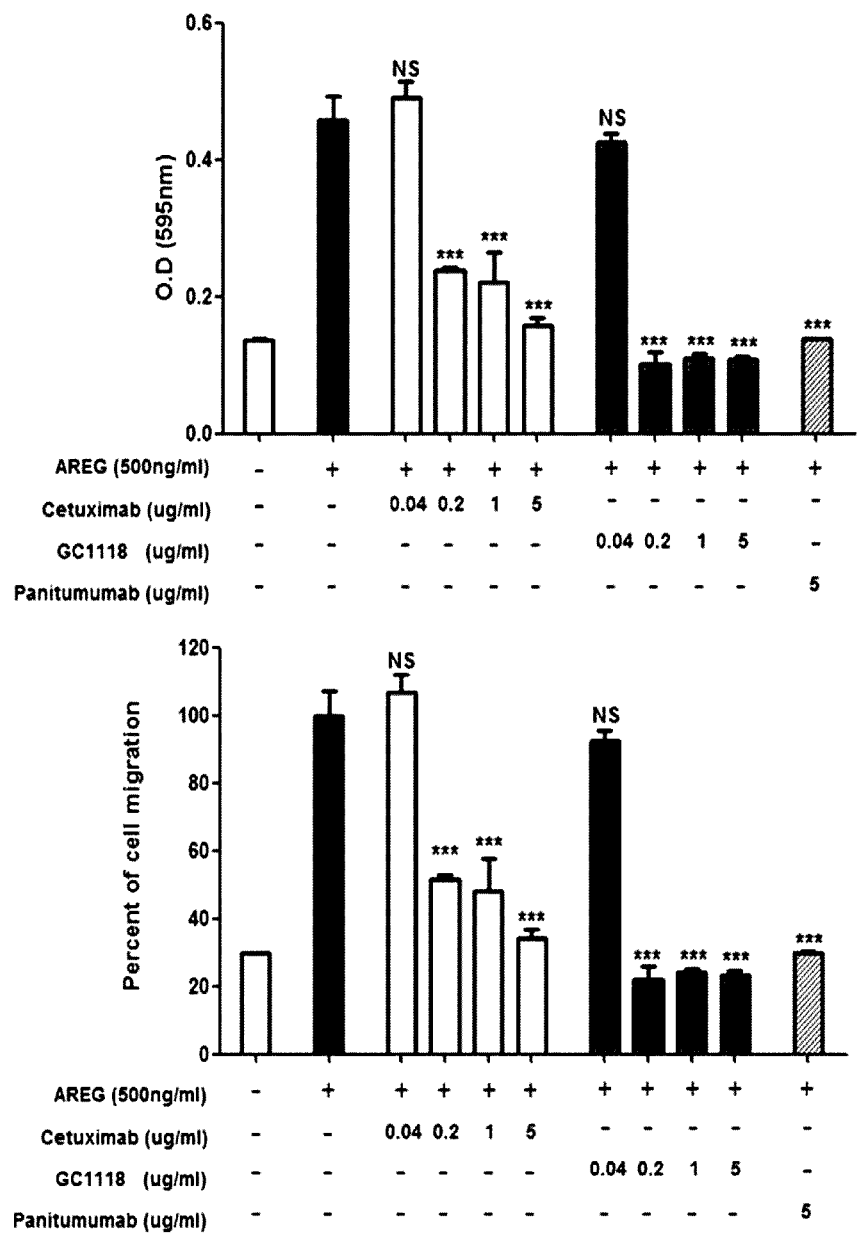

[Fig. 7]
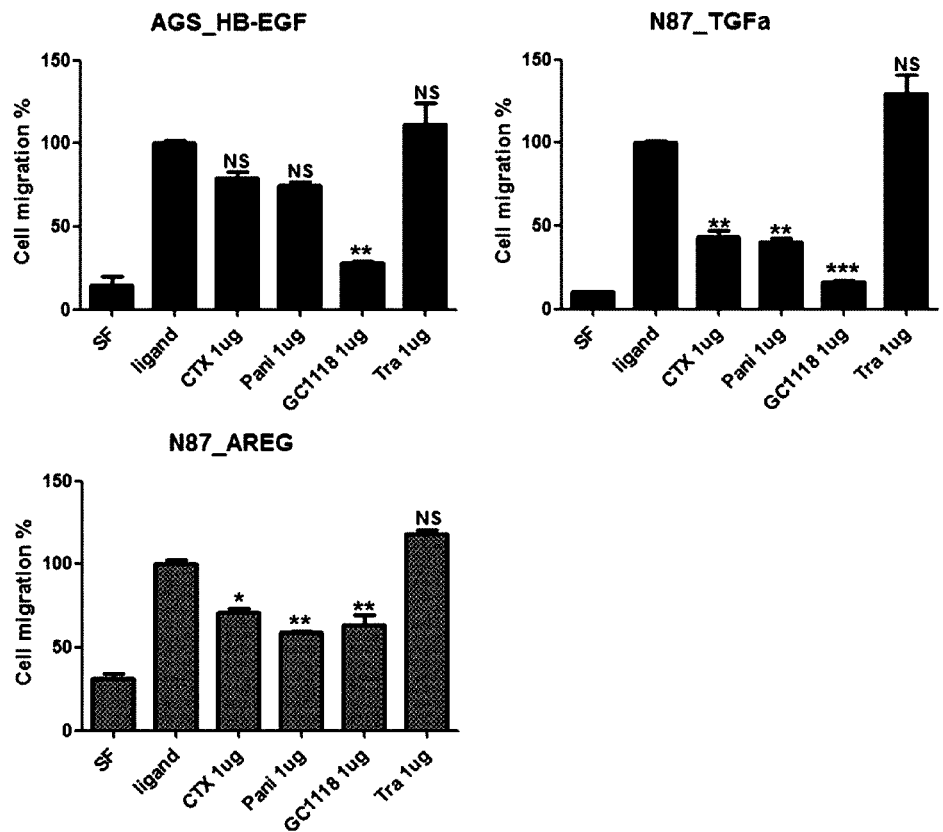

[Fig. 8]
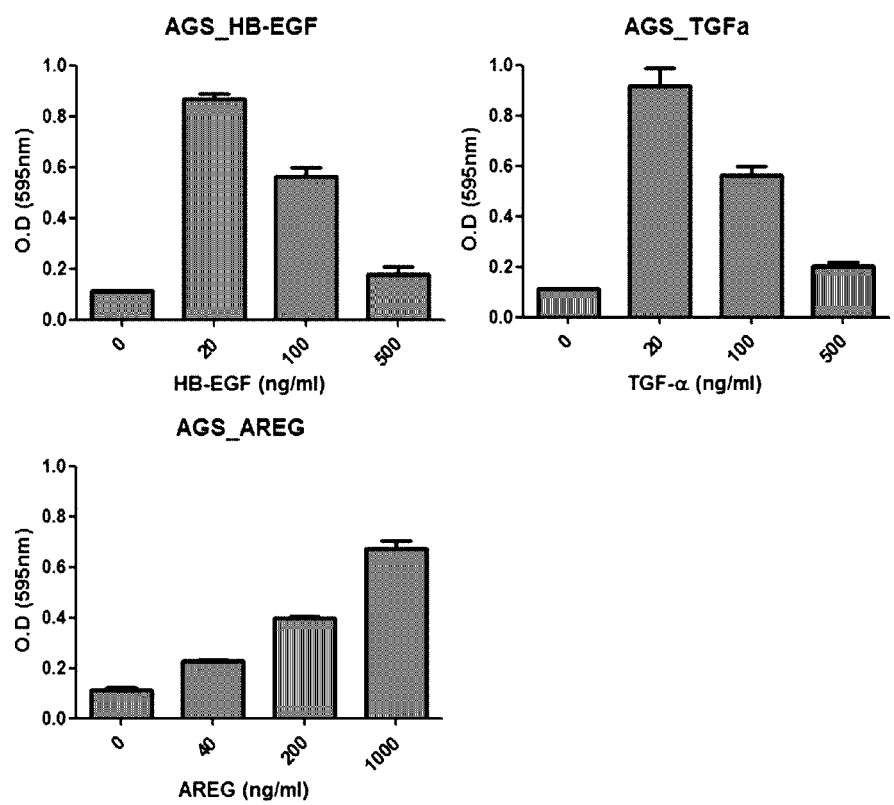

[Fig. 9]
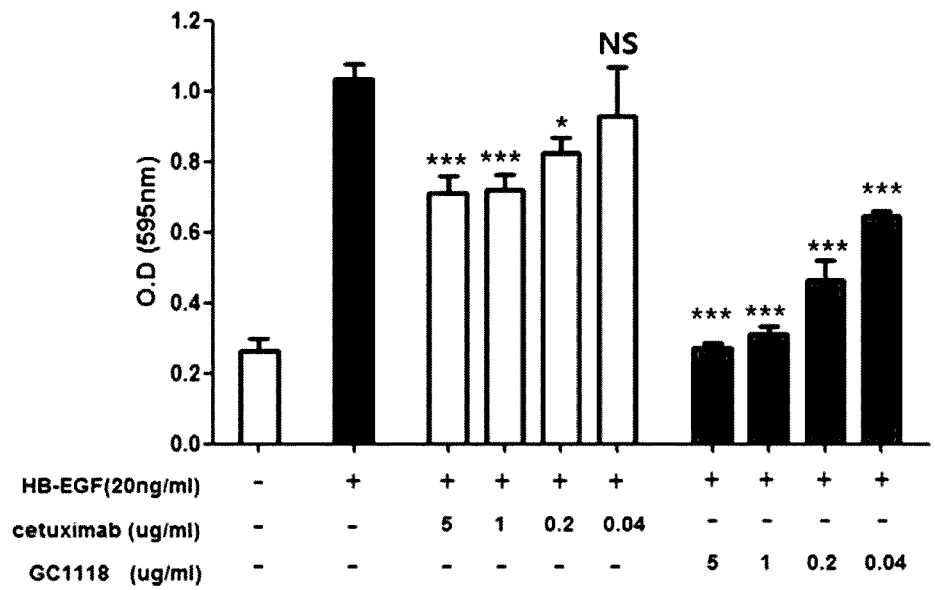
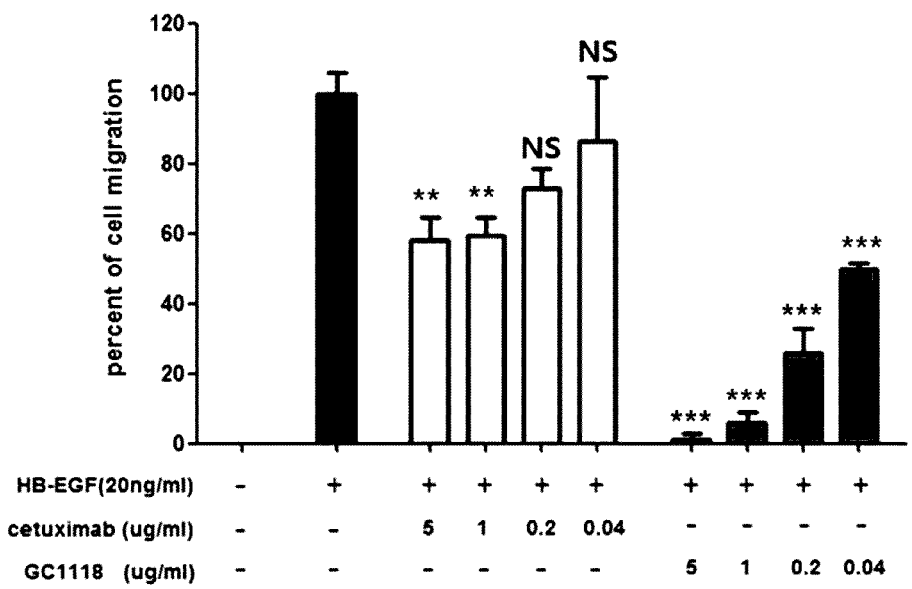

[Fig. 10]
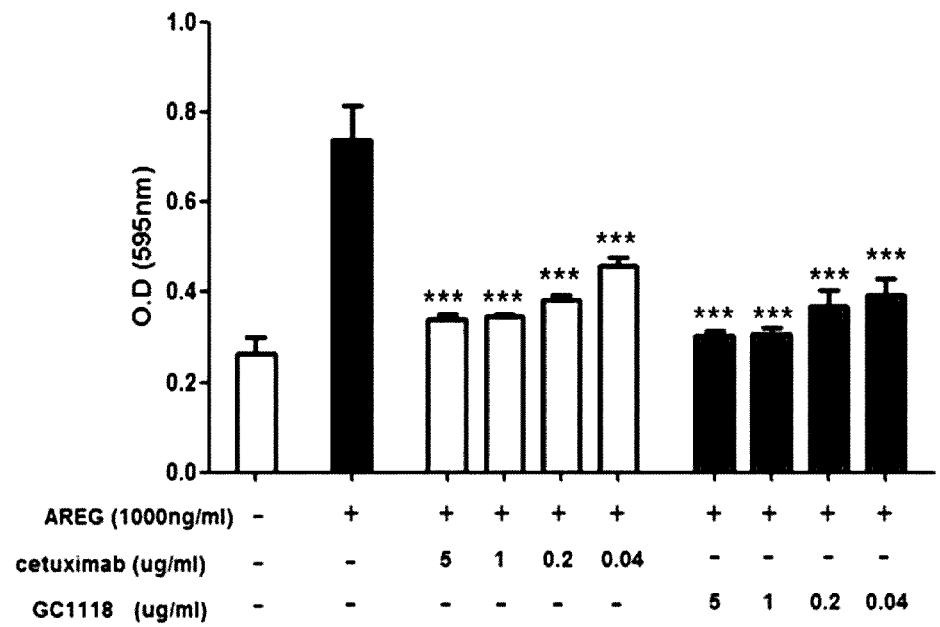
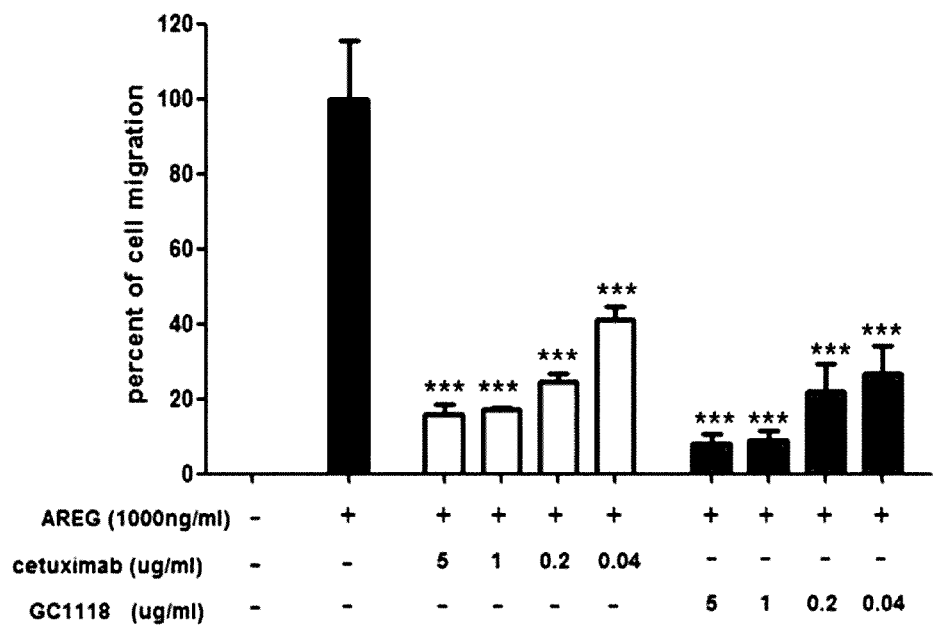

[Fig. 11]
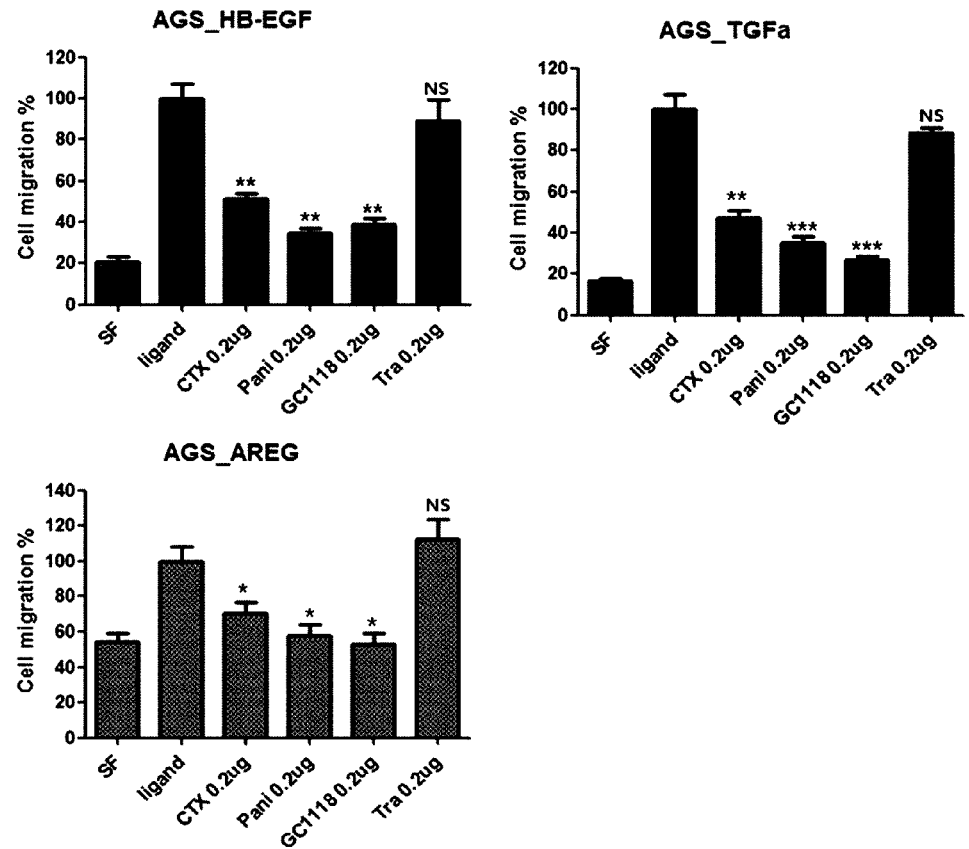
[Fig. 12]
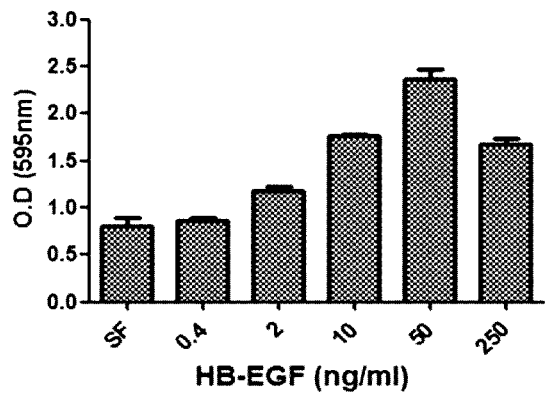

[Fig. 13]
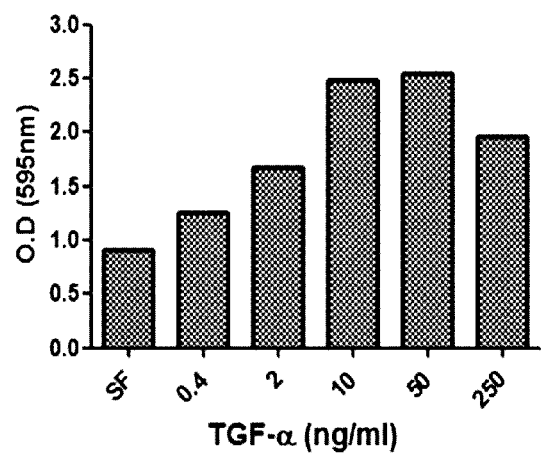
[Fig. 14]
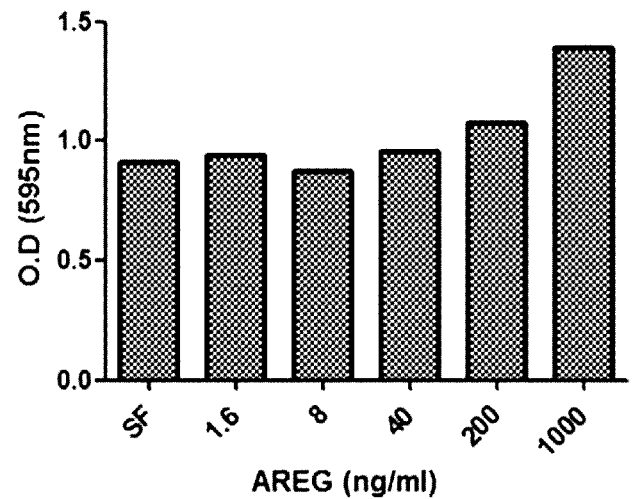

[Fig. 15]
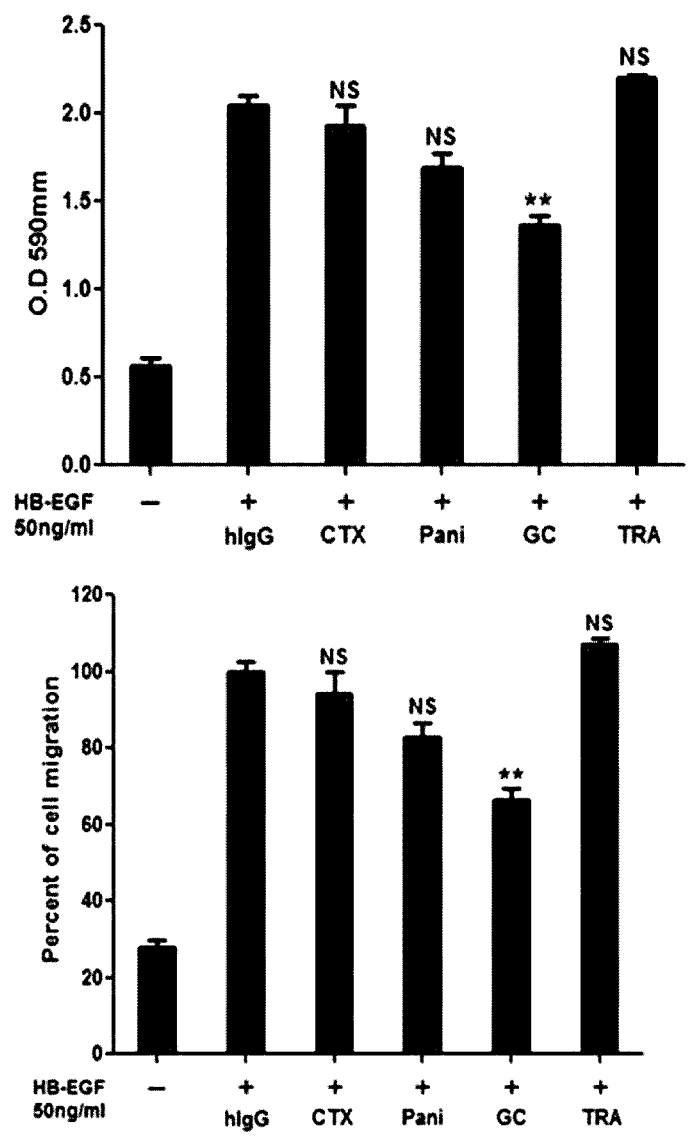

[Fig. 16]
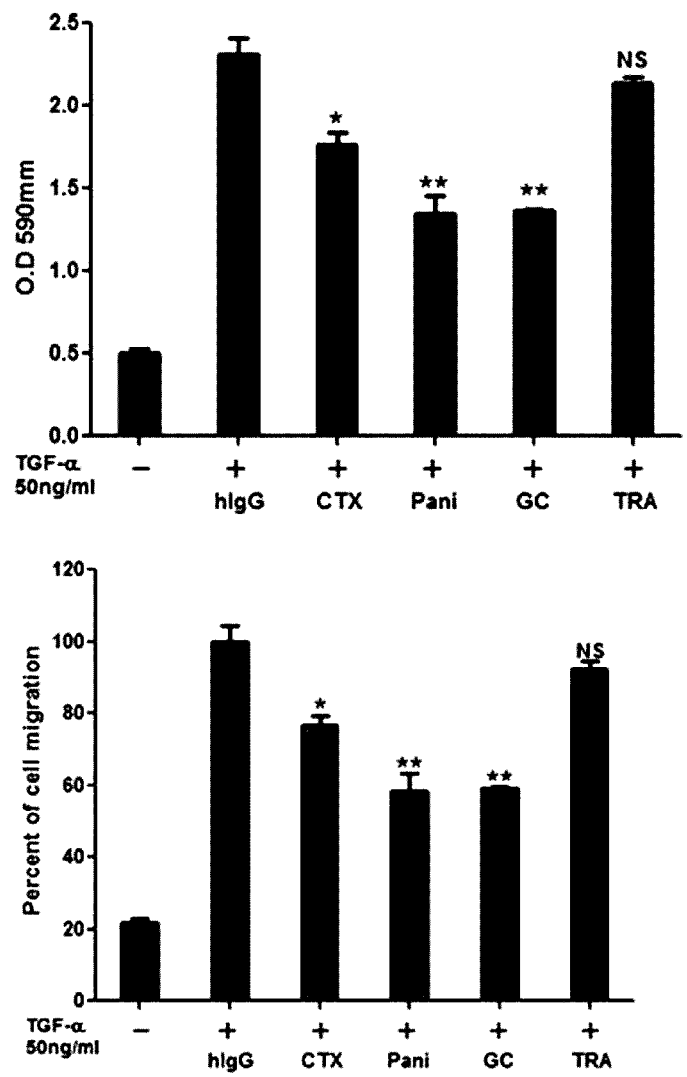

[Fig. 17]
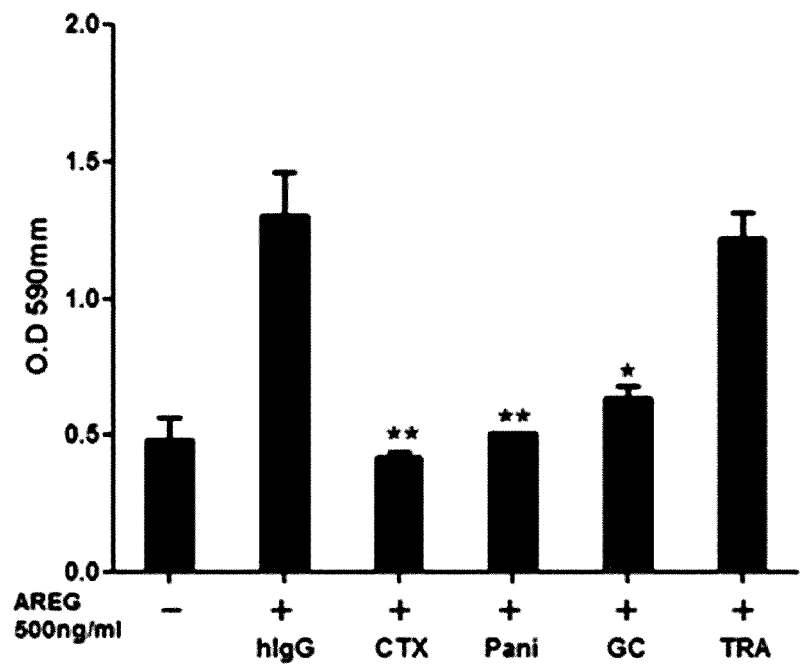
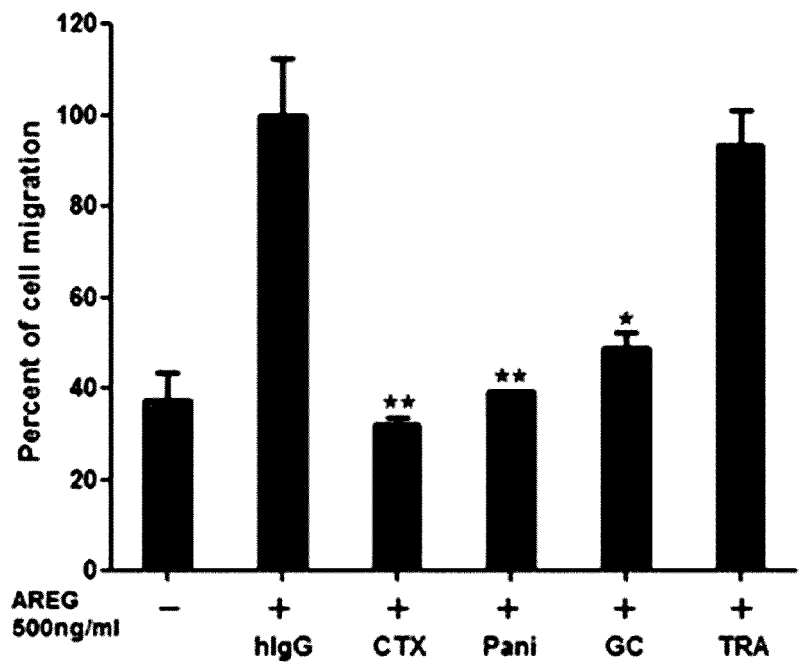

[Fig. 18]
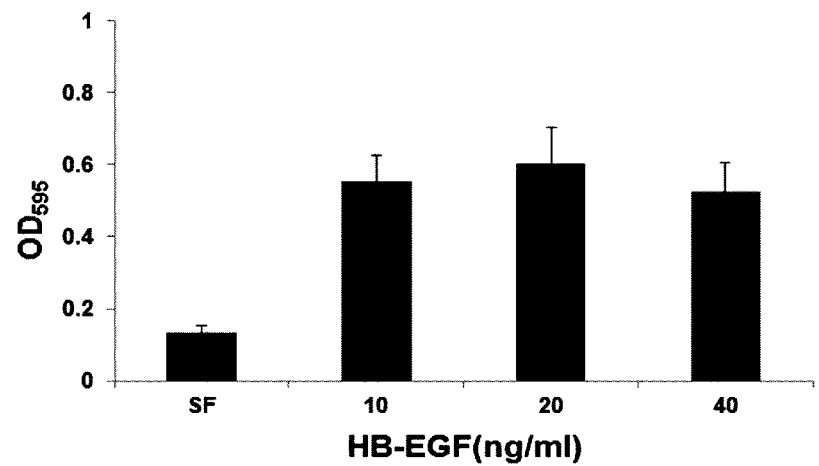
[Fig. 19]
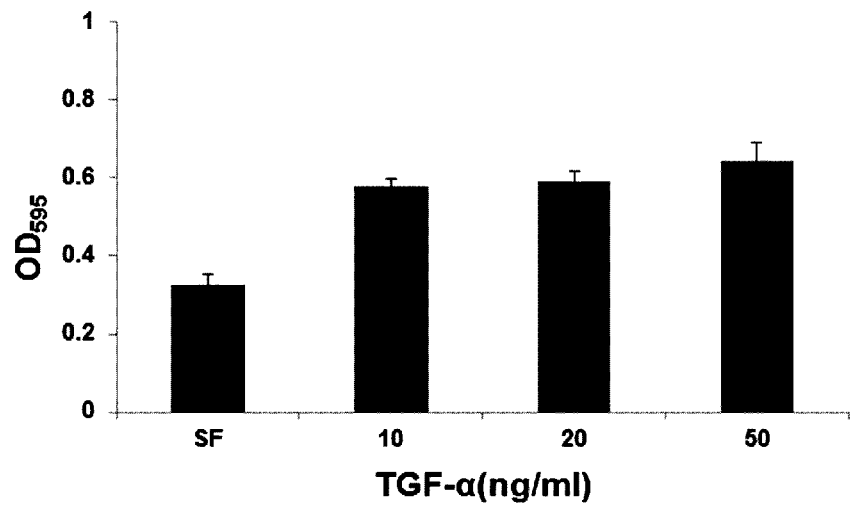

[Fig. 20]
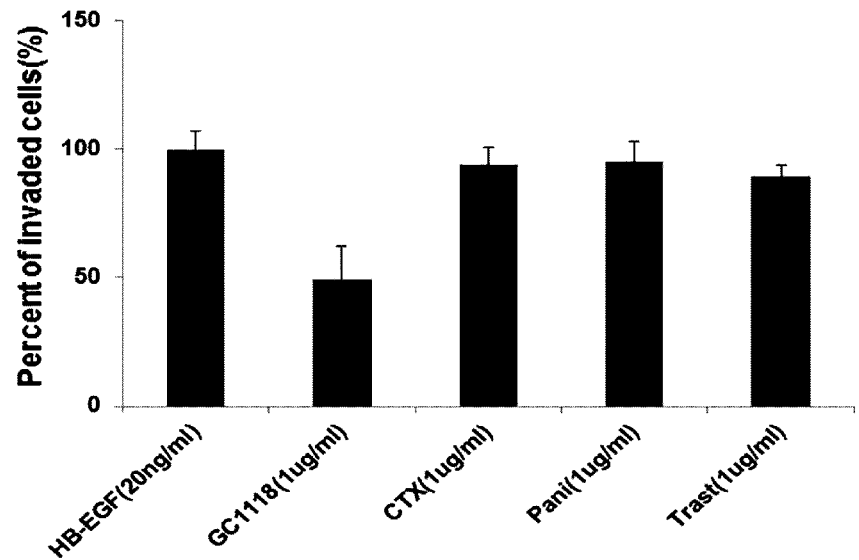
[Fig. 21]
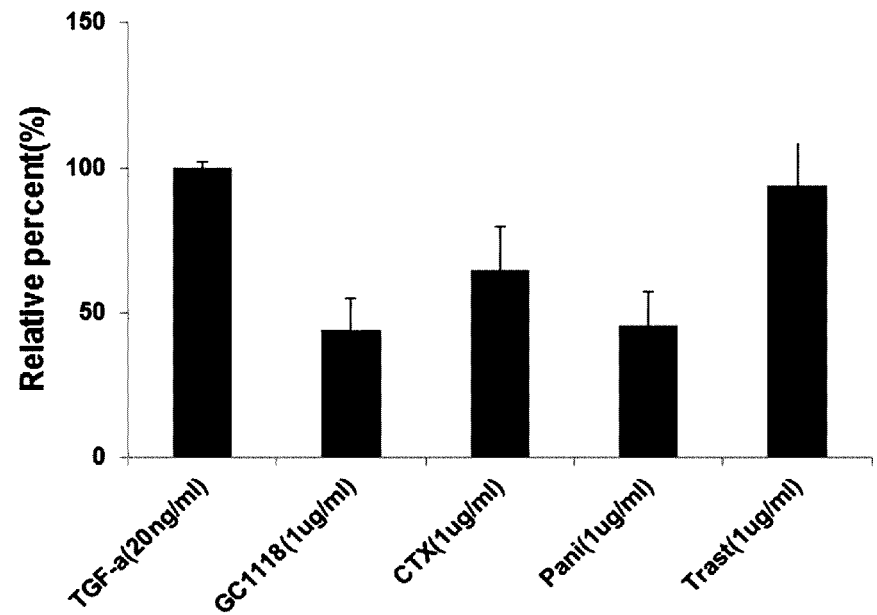

[Fig. 22]
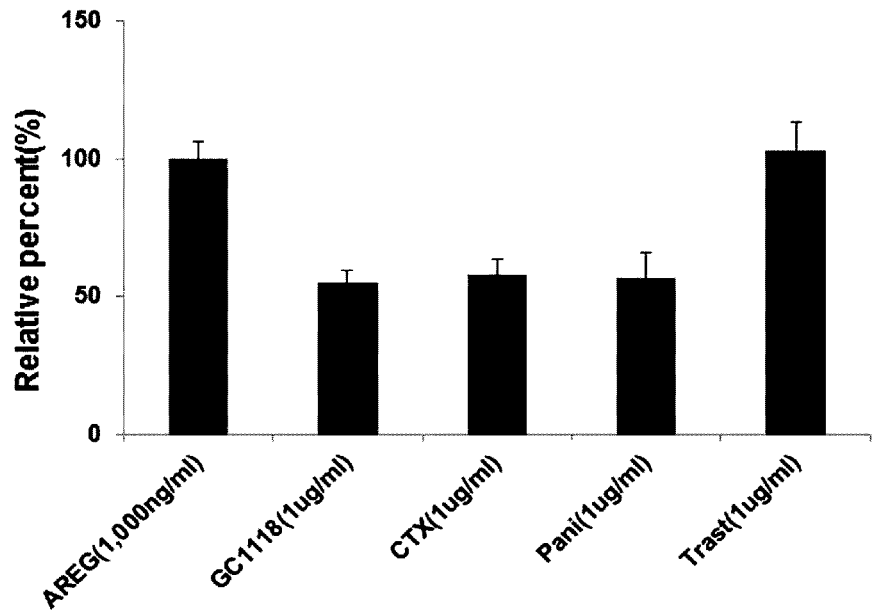
[Fig. 23]
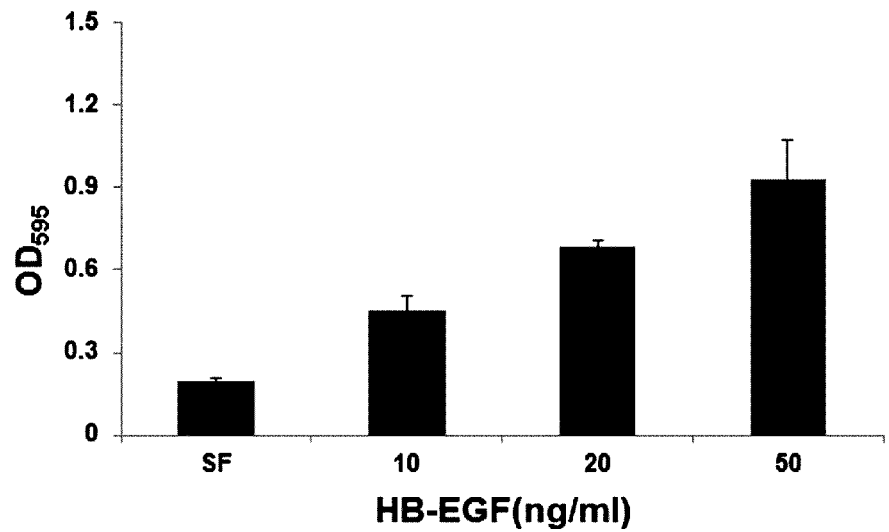

[Fig. 24]
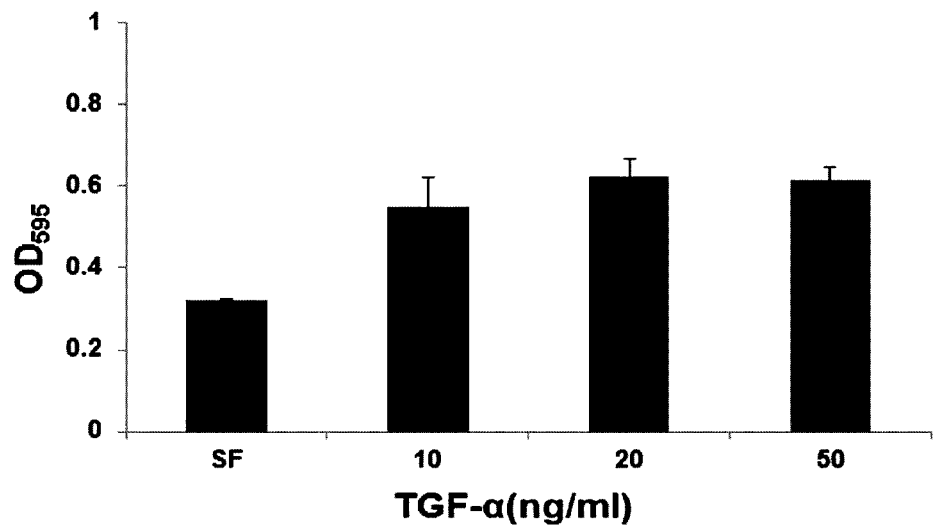
[Fig. 25]
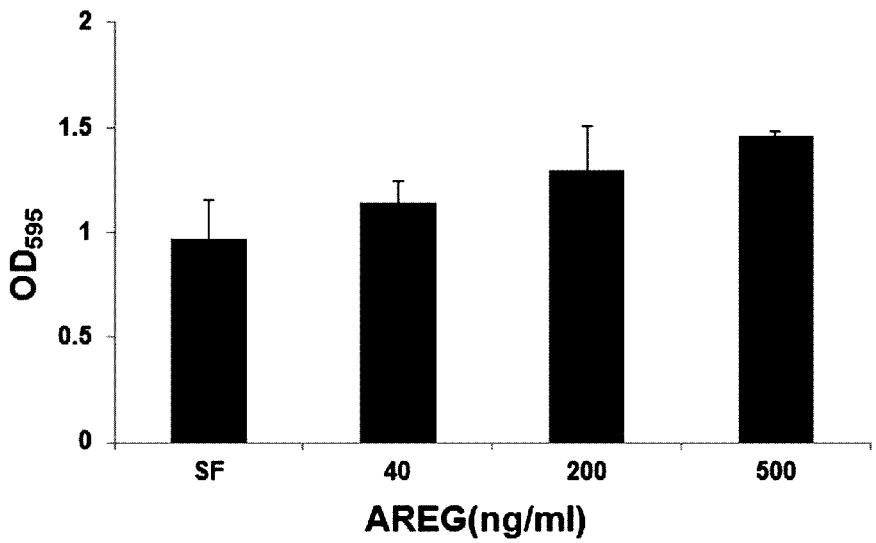

[Fig. 26]
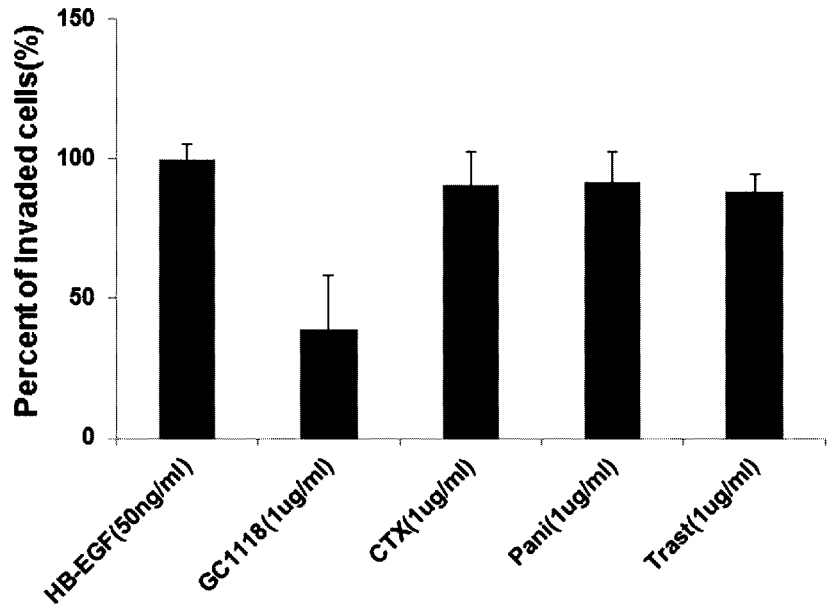
[Fig. 27]
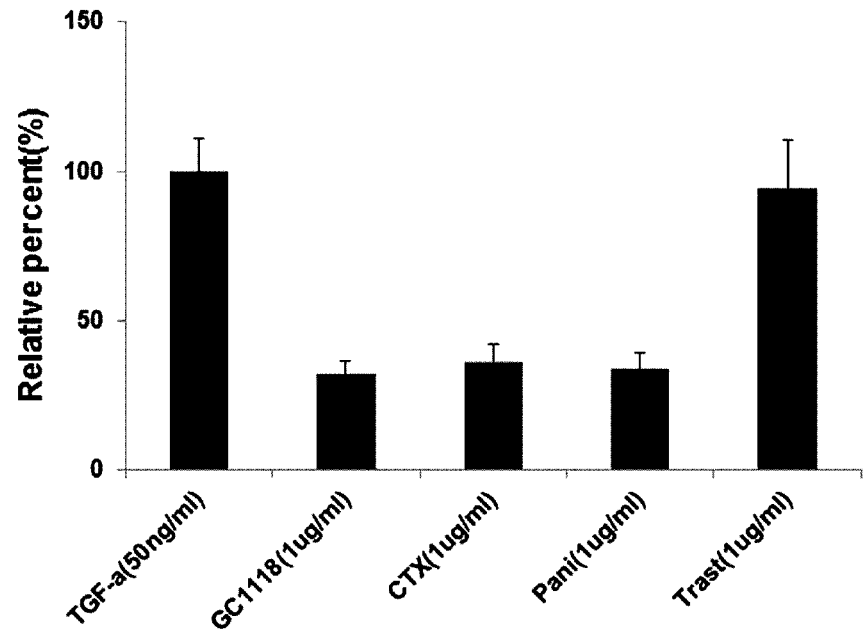

[Fig. 28]
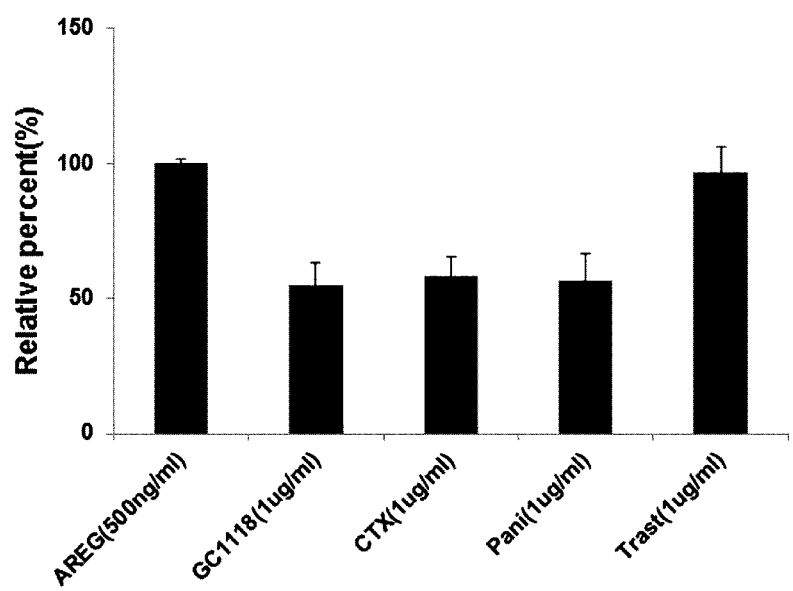

SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: CDR 1 of heavy chain variable region of human
      antibody

<400> SEQUENCE: 1

Asp Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: CDR 2 of heavy chain variable region of human
      antibody

<400> SEQUENCE: 2

Gly Ile Leu Gly Gly Ser Glu Arg Ser Tyr Tyr Arg Asp Ser Val Lys
1               5                   10                  15

Gly

```
<210> SEQ ID NO 3
<211> LENGTH: 10
<212> TYPE: PRT
<213> ORGANISM: Artificial Sequence
<220> FEATURE:
<223> OTHER INFORMATION: CDR 3 of heavy chain variable region of human
      antibody

<400> SEQUENCE: 3

His Gly Ser Pro Gly Tyr Thr Leu Tyr Ala
1               5                   10

<210> SEQ ID NO 4
<211> LENGTH: 16
<212> TYPE: PRT
<213> ORGANISM: Artificial Sequence
<220> FEATURE:
<223> OTHER INFORMATION: CDR 1 of light chain variable region of human
      antibody

<400> SEQUENCE: 4

Arg Ser Asn Gln Asp Leu Thr His Ser Asn Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR 2 of light chain variable region of human
      antibody

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR 3 of light chain variable region of human
      antibody

<400> SEQUENCE: 6

Met Gln Gly Thr His Trp Pro Trp Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Heavy chain variable region of human antibody

<400> SEQUENCE: 7

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Ile Arg Gln Ala Pro Gly Lys Gly Leu Glu Trp Val
        35                  40                  45

Ser Gly Ile Leu Gly Gly Ser Glu Arg Ser Tyr Tyr Arg Asp Ser Val
    50                  55                  60
```

```
Lys Gly Arg Phe Thr Ile Ser Arg Asp Asn Ser Arg Lys Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Ser Pro Gly Tyr Thr Leu Tyr Ala Trp Asp Tyr Trp
            100                 105                 110

Gly Gln Gly Thr Thr Val Thr Val Ser Ser
            115                 120

<210> SEQ ID NO 8
<211> LENGTH: 113
<212> TYPE: PRT
<213> ORGANISM: Artificial Sequence
<220> FEATURE:
<223> OTHER INFORMATION: Light chain variable region of human antibody

<400> SEQUENCE: 8

Asp Ile Val Met Thr Gln Thr Pro Leu Ser Leu Pro Val Thr Pro Gly
  1               5                  10                  15

Glu Pro Ala Ser Ile Ser Cys Arg Ser Asn Gln Asp Leu Thr His Ser
                 20                  25                  30

Asn Gly Asn Thr Tyr Leu Glu Trp Tyr Leu Gln Lys Pro Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Val Gly Val Tyr Tyr Cys Met Gln Gly
                 85                  90                  95

Thr His Trp Pro Trp Thr Phe Gly Gln Gly Thr Lys Val Asp Ile Lys
            100                 105                 110

Arg

<210> SEQ ID NO 9
<211> LENGTH: 16
<212> TYPE: PRT
<213> ORGANISM: Artificial Sequence
<220> FEATURE:
<223> OTHER INFORMATION: CDR 1 of light chain variable region of human
      antibody

<400> SEQUENCE: 9

Arg Ser Ser Gln Ser Val Asp Met Gly Ile Gly Asn Asn Tyr Leu Glu
  1               5                  10                  15

<210> SEQ ID NO 10
<211> LENGTH: 113
<212> TYPE: PRT
<213> ORGANISM: Artificial Sequence
<220> FEATURE:
<223> OTHER INFORMATION: Light chain variable region of human antibody

<400> SEQUENCE: 10

Asp Ile Val Met Thr Gln Thr Pro Leu Ser Leu Pro Val Thr Pro Gly
  1               5                  10                  15

Glu Pro Ala Ser Ile Ser Cys Arg Ser Ser Gln Ser Val Asp Met Gly
                 20                  25                  30

Ile Gly Asn Asn Tyr Leu Glu Trp Tyr Leu Gln Lys Pro Gly Gln Ser
             35                  40                  45

Pro Arg Leu Leu Ile Tyr Lys Val Ser Asn Arg Phe Ser Gly Val Pro
```

```
                       50                  55                  60
Asp Arg Phe Ser Gly Ser Gly Ala Gly Thr Asp Phe Thr Leu Arg Ile
 65                  70                  75                  80

Ser Arg Val Glu Ala Glu Asp Val Gly Val Tyr Tyr Cys Met Gln Gly
                 85                  90                  95

Thr His Trp Pro Trp Thr Phe Gly Gln Gly Thr Lys Val Asp Ile Lys
                100                 105                 110

Arg

<210> SEQ ID NO 11
<211> LENGTH: 330
<212> TYPE: PRT
<213> ORGANISM: Artificial Sequence
<220> FEATURE:
<223> OTHER INFORMATION: Heavy chain constant region of human antibody

<400> SEQUENCE: 11

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 106
<212> TYPE: PRT
<213> ORGANISM: Artificial Sequence
<220> FEATURE:
<223> OTHER INFORMATION: Light chain constant region of human antibody

<400> SEQUENCE: 12

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

PHARMACEUTICAL COMPOSITION FOR INHIBITING METASTASIS OF CANCER, COMPRISING, AS ACTIVE INGREDIENT, ANTIBODY THAT SPECIFICALLY BINDS TO EPIDERMAL GROWTH FACTOR RECEPTOR

CROSS REFERENCE TO RELATED APPLICATIONS

This application is a National Stage of International Application No. PCT/KR2016/004418 filed Apr. 27, 2016.

TECHNICAL FIELD

The present invention relates to a pharmaceutical composition for inhibiting metastasis of cancer comprising an antibody that specifically binds to an epidermal growth factor receptor as an active ingredient, and a method for inhibiting metastasis of cancer using the composition.

BACKGROUND ART

If cancer is formed in one tissue and moves to another tissue as it grows, it is called metastasis. Once the metastasis occurs, the treatment is not only ineffective, but there is a high possibility of recurrence. The process of metastasis of cancer is composed of the steps of migration, adhesion, invasion, etc., and inhibition of either one of the steps can inhibit metastasis of cancer.

Meanwhile, the epidermal growth factor receptor (EGFR) is a type 1 membrane protein of 170 kDa, which is overexpressed in various types of tumors. It has been reported that the EGFR is activated through binding with the ligands EGF (epidermal growth factor) and TGF-α (tumor growth factor-α) to induce proliferation of tumor cells. Thus, EGFR has been investigated as a target for inhibiting tumor proliferation.

However, it is not known whether antibodies capable of targeting the EGFR can be used to inhibit metastasis of cancer. Accordingly, the present inventors have confirmed that the antibody targeting the EGFR inhibits the invasion of a gastric cancer cell line, and have completed the present invention.

DISCLOSURE OF INVENTION

Technical Problem

It is an object of the present invention to provide a pharmaceutical composition for inhibiting metastasis of cancer comprising an antibody specifically binding to an epidermal growth factor receptor as an active ingredient, and a method for inhibiting metastasis of cancer using the composition.

Solution to Problem

To achieve the above objects of the present invention, there is provided a pharmaceutical composition for inhibiting metastasis of cancer comprising an antibody that specifically binds to an epidermal growth factor receptor (EGFR) as an active ingredient, wherein the antibody comprises a) a heavy chain variable region comprising CDR1, CDR2 and CDR3 respectively represented by the amino acid sequences of SEQ ID NO: 1, SEQ ID NO: 2 and SEQ ID NO: 3, a light chain variable region comprising CDR1, CDR2 and CDR3 respectively represented by the amino acid sequences of SEQ ID NO: 4, SEQ ID NO: 5 and SEQ ID NO: 6, a heavy chain constant region, and a light chain constant region; or b) a heavy chain variable region comprising CDR1, CDR2 and CDR3 respectively represented by the amino acid sequences of SEQ ID NO: 1, SEQ ID NO: 2 and SEQ ID NO: 3, a light chain variable region comprising CDR1, CDR2 and CDR3 respectively represented by the amino acid sequences of SEQ ID NO: 9, SEQ ID NO: 5 and SEQ ID NO: 6, a heavy chain constant region, and a light chain constant region.

Also, the present invention provides a method for inhibiting metastasis of cancer comprising administering the composition of the present invention.

Also, the present invention provides a use of the composition of the present invention for use in preparing a drug for inhibiting metastasis of cancer.

Advantageous Effects of Invention

A composition for inhibiting metastasis of cancer or a method for inhibiting metastasis of cancer according to the present invention is effective for inhibiting the migration and invasion of various gastric cancer cell lines induced by an EGFR ligand.

Accordingly, the composition or method of the present invention can be effectively used for inhibiting metastasis of cancer.

BRIEF DESCRIPTION OF DRAWINGS

FIG. 1 is a graph showing the degrees of cell migration depending on concentrations of HB-EGF added to the NCI-N87 cell line.

FIG. 2 is a graph showing the degrees of cell migration depending on concentrations of TGF-α added to the NCI-N87 cell line.

FIG. 3 is a graph showing the degrees of cell migration depending on concentrations of AREG added to the NCI-N87 cell line.

FIG. 4 is a graph showing the degrees of cell migration depending on concentrations of GC1118 added to the NCI-N87 cell line in which cell migration was induced by HB-EGF, as compared to the control group.

FIG. 5 is a graph showing the degrees of cell migration depending on concentrations of GC1118 added to the NCI-N87 cell line in which cell migration was induced by TGF-α, as compared to the control group.

FIG. 6 is a graph showing the degrees of cell migration depending on concentrations of GC1118 added to the NCI-N87 cell line in which cell migration was induced by AREG, as compared to the control group.

FIG. 7 is a graph showing the degrees of cell migration when various EGFR or HER2 antibodies were added to the NCI-N87 cell line, as compared to the control group.

FIG. 8 is a graph showing the degrees of cell migration depending on concentrations of HB-EGF, TGF-α or AREG added to the AGS cell line.

FIG. 9 is a graph showing the degrees of cell migration depending on concentrations of GC1118 added to the AGS cell line in which cell migration was induced by HB-EGF, as compared to the control group.

FIG. 10 is a graph showing the degrees of cell migration depending on concentrations of GC1118 added to the AGS cell line in which cell migration was induced by AREG, as compared to the control group.

FIG. 11 is a graph showing the degrees of cell migration when various EGFR or HER2 antibodies were added to the AGS cell line, as compared to the control group.

FIG. 12 is a graph showing the degrees of cell migration depending on concentrations of HB-EGF added to the NUGC3 cell line.

FIG. 13 is a graph showing the degrees of cell migration depending on concentrations of TGF-α added to the NUGC3 cell line.

FIG. 14 is a graph showing the degrees of cell migration depending on concentrations of AREG added to the NUGC3 cell line.

FIG. 15 is a graph showing the degrees of cell migration when various EGFR or HER2 antibodies were added to the NUGC3 cell line in which cell migration was induced by HB-EGF, as compared to the control group.

FIG. 16 is a graph showing the degrees of cell migration when various EGFR or HER2 antibodies were added to the NUGC3 cell line in which cell migration was induced by TGF-α, as compared to the control group.

FIG. 17 is a graph showing the degrees of cell migration when various EGFR or HER2 antibodies were added to the NUGC3 cell line in which cell migration was induced by AREG, as compared to the control group.

FIG. 18 is a graph showing the degrees of cell invasion depending on concentrations of HB-EGF added to the AGS cell line.

FIG. 19 is a graph showing the degrees of cell invasion depending on concentrations of TGF-α added to the AGS cell line.

FIG. 20 is a graph showing the degrees of cell invasion when various EGFR or HER2 antibodies were added to the AGS cell line in which invasion was induced by HB-EGF, as compared to the control group.

FIG. 21 is a graph showing the degrees of cell invasion when various EGFR or HER2 antibodies were added to the AGS cell line in which invasion was induced by TGF-α, as compared to the control group.

FIG. 22 is a graph showing the degrees of cell migration when various EGFR or HER2 antibodies were added to the AGS cell line in which invasion was induced by AREG, as compared to the control group.

FIG. 23 is a graph showing the degrees of cell invasion depending on concentrations of HB-EGF added to the NUGC3 cell line.

FIG. 24 is a graph showing the degrees of cell invasion depending on concentrations of TGF-α added to the NUGC3 cell line.

FIG. 25 is a graph showing the degrees of cell invasion depending on concentrations of AREG added to the NUGC3 cell line.

FIG. 26 is a graph showing the degrees of cell invasion when various EGFR or HER2 antibodies were added to the NUGC3 cell line in which invasion was induced by HB-EGF, as compared to the control group.

FIG. 27 is a graph showing the degrees of cell invasion when various EGFR or HER2 antibodies were added to the NUGC3 cell line in which invasion was induced by TGF-α, as compared to the control group.

FIG. 28 is a graph showing the degrees of cell invasion when various EGFR or HER2 antibodies were added to the NUGC3 cell line in which invasion was induced by AREG, as compared to the control group.

BEST MODE FOR CARRYING OUT THE INVENTION

Hereinafter, the present invention will be described in more detail.

The present invention provides a pharmaceutical composition for inhibiting metastasis of cancer comprising an antibody that specifically binds to an epidermal growth factor receptor (EGFR) as an active ingredient, wherein the antibody comprises a) a heavy chain variable region comprising CDR1, CDR2 and CDR3 respectively represented by the amino acid sequences of SEQ ID NO: 1, SEQ ID NO: 2 and SEQ ID NO: 3, a light chain variable region comprising CDR1, CDR2 and CDR3 respectively represented by the amino acid sequences of SEQ ID NO: 4, SEQ ID NO: 5 and SEQ ID NO: 6, a heavy chain constant region, and a light chain constant region; or b) a heavy chain variable region comprising CDR1, CDR2 and CDR3 respectively represented by the amino acid sequences of SEQ ID NO: 1, SEQ ID NO: 2 and SEQ ID NO: 3, a light chain variable region comprising CDR1, CDR2 and CDR3 respectively represented by the amino acid sequences of SEQ ID NO: 9, SEQ ID NO: 5 and SEQ ID NO: 6, a heavy chain constant region, and a light chain constant region.

Specifically, the antibody may comprise a) a heavy chain variable region represented by the amino acid sequence of SEQ ID NO: 7, a light chain variable region represented by the amino acid sequence of SEQ ID NO: 8, a heavy chain constant region, and a light chain constant region; or b) a heavy chain variable region represented by the amino acid sequence of SEQ ID NO: 7, a light chain variable region represented by the amino acid sequence of SEQ ID NO: 10, a heavy chain constant region, and a light chain constant region. The heavy chain constant region and the light chain constant region may be a heavy chain constant region or light chain constant region of a known human antibody. Specifically, the heavy chain constant region and the light chain constant region may have an amino acid sequence represented by SEQ ID NO: 11 and SEQ ID NO: 12, respectively.

As used herein, the term "metastasis of cancer" means that cancer cells migrate from a primary organ to another organ and proliferate. The migration of cancer cells to other parts of the body includes the growth of cancerous tissue in the primary cancer which directly invades the surrounding organs, and the metastasis of the cancer to other distant organs along the blood vessels or lymphatic vessels.

The composition according to the present invention can be used to inhibit metastasis of cancer. Herein the metastasis may be induced or promoted by an EGFR ligand. The EGFR ligand may be HB-EGF (heparin binding-EGF-like growth factor), TGF-α (transforming growth factor-α), AREG (amphiregulin) or a combination thereof. The cancer may be a solid cancer, which may include lung cancer, breast cancer, colon cancer, stomach cancer, brain cancer, bladder cancer, head and neck cancer, ovarian cancer, prostatic cancer, colorectal cancer, and the like. Specifically, the cancer may be gastric cancer.

Since the composition according to the present invention effectively inhibits metastasis of cancer, the composition of the present invention may further comprise one or more substances known to have an effect of inhibiting metastasis of cancer.

The pharmaceutical composition according to the present invention may further comprise a pharmaceutically acceptable carrier in addition to the antibody of the present invention.

A pharmaceutically acceptable carrier contained in the pharmaceutical composition of the present invention is typically used in the formulation. Examples thereof include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc., but are not limited thereto.

The pharmaceutical composition of the present invention may further comprise one or more pharmaceutically acceptable additives selected from the group consisting of an excipient, a lubricant, a humectant, a sweetener, a flavoring agent, and a preservative. The composition according to the present invention may be formulated according to a conventional method. Specifically, the composition can be formulated by selecting a known method so as to provide rapid, sustained or delayed release of an active ingredient after administration to a mammal. Herein, the formulations may be in the form of solutions, suspensions, syrups or emulsions in oil or aqueous media, or in the form of extracts, powders, granules, tablets or capsules. In addition, a dispersant or a stabilizer may be further comprised. In addition, the composition may be administered as a single therapeutic agent or in combination with other therapeutic agents, and may be administered sequentially or simultaneously with conventional therapeutic agents.

The carrier may be comprised in an amount of about 1 wt % to about 90 wt %, or about 80 wt % to about 89.99 wt % based on the total weight of the pharmaceutical composition of the invention, and the pharmaceutically acceptable additive may be comprised in an amount of about 0.1 wt % to about 20 wt %.

The present invention also provides a method for inhibiting metastasis of cancer, comprising the step of administering the above composition to a subject.

The subject may be a mammal, particularly a human. As for the administration route and dosage of the antibody according to the present invention, it can be administered to a subject in various ways and amounts depending on the condition of a patient and side effects, and the optimal administration method and the range of dosage can be selected by a person skilled in the art. In addition, the antibody may be administered in combination with another drug or a physiologically active substance known to have a therapeutic effect on the disease to be treated, or may be formulated in a form of a combination drug.

When the antibody is administered parenterally, examples thereof include subcutaneous, intraperitoneal, intramuscular, oral, rectal, intravertebral, intrathecal, intravenous administration.

The above administration may be conducted once or more every 2 weeks, specifically in divided doses of once or twice every 2 weeks. More specifically, the administration can be conducted once a week, or once every two weeks. Herein, when administered once a week, the dose may be 1 to 6 mg/kg or 3 to 5 mg/kg of body weight. When administered once every two weeks, the dose may be 3 to 15 mg/kg, 5 to 12 mg/kg, 6 to 10 mg/kg or 7 to 9 mg/kg of body weight.

The present invention also provides a use of the above pharmaceutical composition in preparing a drug for inhibiting metastasis of cancer.

The composition according to the present invention can be used for preparing a drug for inhibiting metastasis of cancer by inhibiting the migration and invasion of cancer promoted by an EGFR ligand. The cancer is solid cancer, and may include lung cancer, breast cancer, colon cancer, stomach cancer, brain cancer, bladder cancer, head and neck cancer, ovarian cancer, prostatic cancer, colorectal cancer, and the like. Specifically, the cancer may be gastric cancer.

MODE FOR THE INVENTION

Hereinafter, the present invention is explained in detail by Examples. The following Examples are intended to further illustrate the present invention without limiting its scope.

Example 1. Screening and Preparation of Anti-EGFR Antibodies

To screen for the antibodies that specifically bind to an EGFR, an antibody gene library was constructed by mixing human bone marrow RNA, human thymus RNA, human spleen RNA, and human B cell RNA. The cDNA was synthesized using an RNA gene isolated from the RNA gene library as a template, and then the cDNA was used as a template to synthesize the antibody DNAs using primers respectively designed for the scFv region, the heavy chain variable region and the light chain variable region. The synthesized antibody DNAs were inserted into the phage display vectors pKS4H (see Green Cross, Korea, Korean Patent No. 10-0635370) to prepare an antibody DNA library. Then, the antibodies binding to an EGFR were selected by a panning technique using the antibody DNA library. Panning was conducted 4 times and the expression of antibodies from the colonies containing the finally selected DNA library were induced. Herein, the expression of the antibodies was measured by ELISA using a 96-well plate coated with an EGFR.

In order to construct immunoglobulins of complete forms using the selected antibody fragments, the antibody expression vectors of Green Cross Inc., pRC13 and pKC12 (antibody expression plasmids into which variable regions of human antibodies against surface antigen of hepatitis B virus can be inserted, Korean Patent No. 10-523732; Deposit No. KCLRF-BP-00054) were used. The antibody fragments inserted into the vectors were introduced into CHO cells and expressed as immunoglobulins of complete forms, and the expressed antibodies were purified by a protein A-agarose column (Amersham Pharmacia Biotech, USA) (specific methods of selection and preparation of antibodies are as described in Korean Patent No. 10-0092401).

As a result, the selected and prepared antibody was named GC1118. The antibody comprises a heavy chain variable region comprising CDR1, CDR2 and CDR3 respectively represented by the amino acid sequences of SEQ ID NO: 1, SEQ ID NO: 2 and SEQ ID NO: 3, a light chain variable region comprising CDR1, CDR2 and CDR3 respectively represented by the amino acid sequences of SEQ ID NO: 4, SEQ ID NO: 5 and SEQ ID NO: 6, a heavy chain constant region represented by the amino acid sequence of SEQ ID NO: 11, and a light chain constant region represented by the amino acid sequence of SEQ ID NO: 12.

I. Examination of Inhibition Effect of Anti-EGFR Antibody on Gastric Cancer Cell Line Migration Experimental Example 1. Examination of Migration Inhibition Effect on NCI-N87 Gastric Cancer Cell Line by Administration of Anti-EGFR Antibody 1-1. Induction of NCI-N87 Gastric Cancer Cell Line Migration by EGFR Ligand Cell migration analysis was conducted to establish the condition in which migration of the cancer cells of NCI-N87 cell line, a gastric cancer cell line, is induced by the EGFR ligand.

First, the NCI-N87 cell line (ATCC, USA) was cultured in RPMI 1640 medium supplemented with 10% fetal bovine serum, 100 U/ml penicillin and 100 μg/ml streptomycin under the condition of 37° C. and 5% $CO_2$. The cultured cells were dispensed until 70% of a T175 flask was filled. After 24 hours, the cells were washed with 1×PBS and the medium was replaced with a serum-free RPMI1640 medium, and the cells were cultured and prepared under the same condition as above.

Meanwhile, 5 μg/ml of type 1 collagen was diluted with 1×PBS, and transwell insert was filled with 250 μl of the diluted collagen and left in a refrigerator for 24 hours. The transwell insert coated with type I collagen was washed with 1 ml of 1×PBS and dried in a clean bench. The prepared NCI-N87 cell line was trypsinized, collected, and resuspended in a serum-free medium, and dispensed at $4×10^6$ cells per transwell insert. In addition, a 24-well plate was filled with 750 μl of serum-free medium, EGFR ligand was added thereto, and transwell inserts were placed therein. Herein, HB-EGF (heparin binding-EGF-like growth factor, 259-HE-250, R&D systems, USA) and TGF-α (transforming growth factor-α, 239-A-100, R&D systems, USA) were added at 0, 20, 100 or 500 ng/ml, while AREG (amphiregulin, 262-AR, R&D Systems, USA) was added at 0, 40, 200 or 1,000 ng/ml. The 24-well plate was incubated for 6 hours under the same condition as above, and then stained to identify cells that were induced to migrate.

Specifically, the medium of the 24-well plate was removed, and 700 μl of 1×PBS was added, and a transwell insert was immersed thereto and washed. 1×PBS was removed, 500 μl of 4% paraformaldehyde was filled therein, and the cells were fixed by immersing the insert for 15 minutes. The paraformaldehyde was removed and the insert was washed again with an equal volume of 1×PBS. After filling with 500 μl of 0.1% crystal violet solution, the insert was immersed for 30 minutes to stain the cells. Thereafter, distilled water was added to a 500 ml beaker, and the insert was washed. The remaining cells inside the washed insert were wiped with a cotton swab. The stained cells were eluted with 100 μl of 10% acetic acid solution and the OD value was measured with an ELISA plate reader at a wavelength of 595 nm. As a result, OD values measured after addition of HB-EGF, TGF-α or AREG as a ligand are shown in FIGS. 1 to 3, respectively.

As shown in FIGS. 1 to 3, the concentrations of HB-EGF, TGF-α and AREG ligands to be added to induce migration of the NCI-N87 cell line was determined to be 20, 20 and 500 ng/ml, respectively.

1-2. Examination of Migration Inhibition Effect of GC1118 Antibody in NCI-N87 Gastric Cancer Cell Line Whose Migration was Induced by HB-EGF NCI-N87 cell line was treated with 20 ng/ml of HB-EGF to induce cell migration. 0.04, 0.2, 1 or 5 mu g/ml of GC1118 or 0.04, 0.2, 1, or 5 μg of cetuximab (CTX; MERCK, USA) and 5 μg/ml of panitumumab (Pani; Amgen, USA) as comparative examples were added thereto. The inhibition of cancer cell migration by GC1118 was examined by the same condition and method as Experimental Example 1-1.

As for the migration inhibition effect, the ratio of migrated cells when treated with each antibody relative to those in the case added with HB-EGF alone was calculated as a percentage of the OD value, and the results were shown in FIG. 4.

As shown in FIG. 4, both GC1118 and cetuximab inhibited the migration of cancer cells in a concentration-dependent manner. Specifically, cetuximab did not inhibit migration at 0.04 μg/ml, but GC1118 inhibited cell migration by 20%. Also, at 5 μg/ml, cetuximab and panitumumab inhibited cancer cell migration by 40%, while GC1118 inhibited by 60%.

1-3. Examination of Migration Inhibition Effect of GC1118 Antibody in NCI-N87 Gastric Cancer Cell Line Whose Migration was Induced by TGF-α

Cell migration was induced by 20 ng/ml of TGF-α instead of HG-EGF, and cetuximab was added as a comparative example, and otherwise, the experiment was conducted by the same condition and method as Experimental Example 1-2.

As for the migration inhibition effect, the ratio of migrated cells when treated with each antibody relative to those in the case added with TGF-α alone was calculated as a percentage of the OD value, and the results were shown in FIG. 5.

As shown in FIG. 5, both GC1118 and cetuximab inhibited the migration of cancer cells in a concentration-dependent manner. Specifically, cetuximab and GC1118 did not show a migration inhibition effect at 0.04 μg/ml, but showed the effect at 5 μg/ml.

1-4. Examination of Migration Inhibition Effect of GC1118 Antibody in NCI-N87 Gastric Cancer Cell Line Whose Migration was Induced by AREG Cell migration was induced by 500 ng/ml of AREG instead of HG-EGF, and otherwise, the experiment was conducted by the same condition and method as Experimental Example 1-2.

As for the migration inhibition effect, the ratio of migrated cells when treated with each antibody relative to those in the case added with AREG alone was calculated as a percentage of the OD value, and the results were shown in FIG. 6.

As shown in FIG. 6, both GC1118 and cetuximab inhibited the migration of cancer cells in a concentration-dependent manner. Specifically, cetuximab and GC1118 did not show a migration inhibition effect at 0.04 μg/ml, but showed the effect at 0.2 μg/ml or more.

1-5. Comparison of Migration Inhibition Effects of GC1118 and Other EGFR Antibodies on Cancer Cells The migration inhibition effects of the GC1118 antibody and other antibodies targeting EGFR or HER2 on cancer cells were compared.

First, 20 ng/ml of HB-EGF or TGF-α, or 500 ng/ml of AREG was added to induce the migration of cancer cells. 1 μg/ml cetuximab, panitumumab, trastuzumab (Trast; Roche, USA) or GC1118 was added thereto, and immunoglobulin was used as a control. Otherwise, the experiment was conducted by the same condition and method as Experimental Example 1-1.

As for the migration inhibition effect, the ratio of migrated cells when treated with each antibody relative to those in the case added with the EGFR ligand alone was calculated as a percentage of the OD value, and the results were shown in FIG. 7.

As shown in FIG. 7, cetuximab, panitumumab and GC1118, antibodies targeting EGFR, inhibited cell migration, but trastuzumab, an antibody targeting HER2, showed little effects. Meanwhile, the cell migration induced by HB-EGF was inhibited only by GC1118, whereas the cell migration induced by TGF-α or AREG did not show differences between EGFR-targeting antibodies.

Experimental Example 2. Examination of Migration Inhibition Effect of Anti-EGFR Antibody on AGS Gastric Cancer Cell Line 2-1. Induction of Migration of AGS Gastric Cancer Cell Line by EGFR Ligand The condition in which the migration of the cancer cells of the AGS cell line (ATCC, USA) are induced by the EGFR ligand was established. $3 \times 10^6$ cells were dispensed into each transwell insert, and otherwise, the experiment was conducted by the same condition and method as Experimental Example 1-1. As a result, the OD values measured after addition of HB-EGF, TGF-α or AREG as a ligand was shown in FIG. 8.

As shown in FIG. 8, the concentrations of HB-EGF, TGF-α and AREG ligands to be added to induce migration of AGS cell lines were determined to be 20, 20 and 500 ng/ml, respectively.

2-2. Examination of Migration Inhibition Effect of GC1118 Antibody in AGS Gastric Cancer Cell Line Whose Migration was Induced by HB-EGF AGS cell line was used, and otherwise, the experiment was conducted by the same condition and method as Experimental Example 1-2. As for the migration inhibition effect, the ratio of migrated cells when treated with each antibody relative to those in the case added with HB-EGF alone was calculated as a percentage of the OD value, and the results were shown in FIG. 9.

As shown in FIG. 9, GC1118 showed superior migration inhibition effect on the AGS cell line as compared to cetuximab. Specifically, cetuximab did not show migration inhibition effects at 0.04 and inhibited the migration of cancer cells by about 40% at 5 Meanwhile, GC1118 inhibited the migration of cancer cells by 40% and 90% at 0.04 and 5 respectively.

2-3. Examination of Migration Inhibition Effect of GC1118 Antibody in AGS Gastric Cancer Cell Line Whose Migration was Induced by AREG In the AGS gastric cancer cell line, the cell migration was induced by 1,000 ng/ml of AREG, and otherwise, the experiment was conducted by the same condition and method as Experimental Example 1-4. As for the migration inhibition effect, the ratio of migrated cells when treated with each antibody relative to those in the case added with AREG alone was calculated as a percentage of the OD value, and the results were shown in FIG. 10.

As shown in FIG. 10, both GC1118 and cetuximab inhibited the migration of cancer cells in a concentration-dependent manner. Specifically, both antibodies showed superior migration effect on the cancer cells by 60% even at 0.04 μg/ml.

2-4. Comparison of Migration Inhibition Effect of GC1118 Antibody and Other EGFR Antibodies on Cancer Cells Cetuximab, panitumumab, trastuzumab or GC1118 at a concentration of 0.2 μg/ml was added, and otherwise, the experiment was conducted by the same condition and method as Experimental Example 1-5. As for the migration inhibition effect, the ratio of migrated cells when treated with each antibody relative to those in the case added with an EGFR ligand alone was calculated as a percentage of the OD value, and the results were shown in FIG. 11.

As shown in FIG. 11, cetuximab, panitumumab and GC1118, antibodies targeting the EGFR, inhibited the cell migration, but trastuzumab, an antibody targeting HER2, did not show inhibition effects. Meanwhile, as a result of cell staining, GC1118 led to fewer number of migrated cells than cetuximab or panitumumab, but the OD value was not significantly different from other antibodies. It seems that the number of migrated cells was too small to produce a significant difference in OD values.

Experimental Example 3. Examination of Inhibition on Migration of NUGC3 Gastric Cancer Cell Line by EGFR Ligand 3-1. Induction of NUGC3 Gastric Cancer Cell Line Migration by EGFR Ligand The condition in which the migration of the cancer cells of the NUGC3 cell line (ATCC, USA) are induced by the EGFR ligand was established. $2 \times 10^6$ cells were dispensed into each transwell insert, and HB-EGF and TNF-α were added at 0, 0.4, 2, 10, 50 and 250 ng/ml, while AREG was added at 0, 1.6, 8, 40, 200 and 1,000 ng/ml. And otherwise, the experiment was conducted by the same condition and method as Experimental Example 1-1. As a result, the OD values measured after addition of HB-EGF, TGF-α or AREG as a ligand was shown in FIG. 12.

As shown in FIGS. 12 to 14, the concentrations of HB-EGF, TGF-α and AREG ligands to be added to induce migration of the AGS cell line was determined to be 50, 50 and 500 ng/ml, respectively.

3-2. Comparison of Migration Inhibition of GC1118 Antibody in NUGC3 Gastric Cancer Cell Line in which Migration was Induced by HB-EGF In the NUGC3 cell line, cell migration was induced by 50 ng/ml of HB-EGF, and otherwise, the experiment was conducted by the same condition and method as Experimental Example 1-5. As for the migration inhibition effect, the ratio of migrated cells when treated with each antibody relative to those in the case added with the EGFR ligand alone was calculated as a percentage of the OD value, and the results were shown in FIG. 15.

As shown in FIG. 15, cetuximab, panitumumab, and trastuzumab did not inhibit HB-EGF-induced cell migration, but GC1118 inhibited the cell migration by 40%.

3-3. Examination of Migration Inhibition Effect of GC1118 Antibody on the Migration of NUGC3 Gastric Cancer Cells Induced by TGF-α

The cell migration was induced by 50 ng/ml of TGF-α instead of HB-EGF, and otherwise, the experiment was conducted by the same condition and method as Experimental Example 3-2.

As for the migration inhibition effect, the ratio of migrated cells when treated with each antibody relative to those in the case added with the EGFR ligand alone was calculated as a percentage of the OD value, and the results were shown in FIG. 16.

As shown in FIG. 16, cetuximab, panitumumab, trastuzumab and GC1118 inhibited TGF-α induced cell migration, but trastuzumab did not inhibit the cell migration.

3-4. Comparison of Migration Inhibition of GC1118 Antibody in NUGC3 Gastric Cancer Cell Line in which Migration was Induced by AREG The cell migration was induced with 500 ng/ml of AREG instead of HB-EGF, and otherwise, the experiment was conducted by the same condition and method as Experimental Example 3-2.

As for the migration inhibition effect, the ratio of migrated cells when treated with each antibody relative to those in the case added with the EGFR ligand alone was calculated as a percentage of the OD value, and the results were shown in FIG. 17.

As shown in FIG. 17, cetuximab, panitumumab, trastuzumab and GC1118, antibodies targeting the EGFR, inhibited cell migration, but trastuzumab, an antibody targeting HER2, did not show the inhibition effect.

II. The Inhibition Effect of Anti-EGFR Antibody on Metastasis of Gastric Cancer Cell Line Experimental Example 4. Examination of Inhibition Effect of Anti-EGFR Antibody Administration on Metastasis of AGS Gastric Cancer Cell Line 4-1. Induction of Invasion of AGS Cancer Cell by EGFR Ligand Matrigel chamber analysis was conducted to establish the condition under which invasion of the AGS cell line, a gastric cancer cell line, was induced by the EGFR ligand.

First, the AGS cell line, a gastric cell line, was cultured in RPMI 1640 medium supplemented with 10% fetal bovine serum, 100 U/ml penicillin and 100 µg/ml streptomycin under the condition of 37° C. and 5% $CO_2$. The cultured cells were divided into 60% of a T175 flask. After 24 hours, the cells were washed with 1×PBS, and replaced with serum-free RPMI1640 medium, and cultured under the same conditions as above.

Meanwhile, the Matrigel chamber (Cat. No. 354483, Corning, USA) was filled with the RPMI1640 medium (invasion medium) supplemented with 0.5 ml of fetal bovine serum, which was then rehydrated for 2 hours, and then the medium was removed. The prepared cells were collected by trypsinization, and resuspended in a serum-free medium supplemented with 0.1% bovine serum albumin. A 24-well plate was filled with 750 µl of the invasion medium, and HB-EGF and TGF-α were added at 10, 20 or 50 ng/ml. The chamber was placed on a 24-well plate containing 500 µl of the invasion medium, and the resuspended cells were added at $3×10^6$ cells per chamber. The cells were cultured under the same conditions as above for 24 hours, and then stained to identify invasion-induced cells.

Specifically, the medium of the 24-well plate was removed, 500 µl of 1×PBS was added thereto, and the chamber was then immersed and washed. 1×PBS was removed, the 24-well plate was filled with 500 µl of 4% paraformaldehyde, and immersed for 10 minutes to fix the cells. Paraformaldehyde was removed and 500 µl of a 0.1% crystal violet solution was filled, and the chamber was immersed for 10 minutes to stain the cells. Thereafter, distilled water was added to a 500 ml beaker, and the chamber was washed. Noninvasive cells inside the washed chamber were wiped with a cotton swab, which were then dried at room temperature for 1 hour. In addition, the stained cells were eluted with 100 µl of 10% acetic acid solution, and the OD value was measured with an ELISA plate reader at a wavelength of 595 nm. As a result, OD values measured after addition of HB-EGF and TGF-α as ligands are shown in FIGS. 18 and 19, respectively.

As shown in FIGS. 18 and 19, the invasion of the AGS cell line was induced by HB-EGF and TGF-α ligands. When HB-EGF was added at 10, 20, and 50 ng/ml, the invasion was increased by 4.1, 4.5, and 3.9-fold, respectively, as compared to the control. When TGF-α was added at the same concentrations, invasion was increased by 1.8, 1.8, and 1.9-fold, respectively, as compared to the control.

4-2. Examination of Invasion Inhibition Effect of GC1118 Antibody in AGS Gastric Cancer Cell Line in which Invasion was Induced by HB-EGF The invasion was induced by 20 ng/ml of HB-EGF, and otherwise, the experiment was conducted by the same condition and method as Experimental Example 4-1. Herein, 1 µg/ml of GC1118 was added as an experimental group, and 1 µg/ml of cetuximab, 1 µg/ml of panitumumab, and 1 µg/ml of trastuzumab were used as comparative examples. The experiment was repeated three times with two sets, and the average values were shown.

As for the invasion inhibition effect, the ratio of invaded cells when treated with each antibody relative to those in the case added with HG-EGF alone was calculated as a percentage of the OD value, and the results were shown in Table 1 and FIG. 20.

TABLE 1

|  | HB-EGF (20 ng/ml) | GC1118 (1 µg/ml) | Cetuximab (1 µg/ml) | Panitumumab (1 µg/ml) | Trastuzumab (1 µg/ml) |
|---|---|---|---|---|---|
| 1-1 | 99.3 | 50.6 | 101.0 | 98.8 | 87.4 |
| 1-2 | 100.7 | 56.8 | 93.8 | 98.5 | 93.6 |
| 2-1 | 100.3 | 57.7 | 91.8 | 92.2 | 83.1 |
| 2-2 | 99.7 | 64.2 | 102.9 | 106.8 | 86.4 |
| 3-1 | 111.7 | 33.3 | 88.6 | 83.2 | 95.3 |
| 3-2 | 88.3 | 34.9 | 86.2 | 92.5 | 91.3 |
| Average (%) | 100.0 | 49.6 | 94.0 | 95.3 | 89.5 |
| Standard deviation | 7.4 | 12.8 | 6.7 | 8.0 | 4.7 |

As shown in Table 1 and FIG. 20, GC1118 showed excellent effect of inhibiting the invasion of the AGS cell line induced by HB-EGF. Specifically, cetuximab, panitumumab, and trastuzumab inhibited the cell invasion by 6%, 4.7%, and 10.5%, respectively, while GC1118 inhibited by 50.4%.

4-3. Examination of Invasion Inhibition Effect of GC1118 Antibody in AGS Gastric Cancer Cell Line in which Invasion was Induced by TGF-α

The invasion was induced by 20 ng/ml of TGF-α instead of HB-EGF, and otherwise, the experiment was conducted by the same condition and method as Experimental Example 4-2.

As for the invasion inhibition effect, the ratio of invaded cells when treated with each antibody relative to those in the case added with TGF-α alone was calculated as a percentage of the OD value, and the results were shown in Table 2 and FIG. 21.

TABLE 2

|  | TGF-α (20 ng/ml) | GC1118 (1 µg/ml) | Cetuximab (1 µg/ml) | Panitumumab (1 µg/ml) | Trastuzumab (1 µg/ml) |
|---|---|---|---|---|---|
| 1-1 | 98.0 | 45.1 | 78.6 | 37.9 | 110.8 |
| 1-2 | 102.0 | 41.6 | 83.9 | 44.8 | 106.4 |
| 2-1 | 99.7 | 31.2 | 50.1 | 39.0 | 69.4 |
| 2-2 | 100.3 | 33.8 | 46.2 | 33.8 | 90.9 |
| 3-1 | 98.0 | 57.9 | 65.0 | 61.9 | 90.4 |
| 3-2 | 102.0 | 54.8 | 66.0 | 57.9 | 95.4 |
| Average (%) | 100.0 | 44.1 | 66.0 | 45.9 | 93.9 |
| Standard deviation | 1.83 | 10.82 | 14.93 | 11.50 | 14.62 |

As shown in Table 2 and FIG. 21, GC1118 showed the excellent effect of inhibiting the invasion of AGS cell line induced by TGF-α. Specifically, cetuximab and trastuzumab inhibited the cell invasion by 35% and 6.1%, respectively, but GC1118 inhibited by 55.9%, similar to panitumumab which inhibited cell invasion by 54.1%.

4-4. Examination of Invasion Inhibition Effect of GC1118 Antibody in AGS Gastric Cancer Cell Line in which Invasion was Induced by AREG The invasion was induced by 1000 ng/ml of AREG instead of HB-EGF, and the experiment was repeated twice with two sets, and otherwise, the experiment was conducted by the same condition and method as Experimental Example 4-2.

As for the invasion inhibition effect, the ratio of invaded cells when treated with each antibody relative to those in the case added with AREG alone was calculated as a percentage of the OD value, and the results were shown in Table 3 and FIG. 22.

TABLE 3

|  | AREG (1,000 ng/ml) | GC1118 (1 µg/ml) | Cetuximab (1 µg/ml) | Panitumumab (1 µg/ml) | Trastuzumab (1 µg/ml) |
|---|---|---|---|---|---|
| 1-1 | 93.8 | 55.3 | 65.2 | 68.8 | 93.8 |
| 1-2 | 106.2 | 61.3 | 60.3 | 58.4 | 107.0 |
| 2-1 | 95.4 | 51.8 | 54.2 | 51.5 | 96.7 |
| 2-2 | 104.6 | 53.1 | 52.3 | 49.9 | 115.5 |
| Average (%) | 100.0 | 55.4 | 58.0 | 57.2 | 103.3 |
| Standard deviation | 6.34 | 4.21 | 5.87 | 8.62 | 9.96 |

As shown in Table 3 and FIG. 22, GC1118 showed the excellent effect of inhibiting the invasion of AGS cell line induced by AREG. Specifically, GC1118 inhibited the cell invasion by 44.6%, which was similar to the level of inhibition of the control group, cetuximab (42%) or panitumumab (42.8%).

Experimental Example 5. Examination of Inhibition Effect of Anti-EGFR Antibody Administration on Metastasis of NUGC3 Gastric Cancer Cell Line 5-1. Induction of Invasion of NUGC3 Cancer Cell by EGFR Ligand Matrigel chamber analysis was conducted to establish the condition under which invasion of the NUGC3 cell line, a gastric cancer cell line, was induced by the EGFR ligand. For the invasion induction, 10, 20 or 50 ng/ml of HB-EGF and TGF-α, and 40, 200 and 500 ng/ml of AREG, which are EGFR ligands, were added. Otherwise, the experiment was conducted by the same condition and method as Experimental Example 4-1. As a result, OD values measured after addition of HB-EGF, TGF-α and AREG as the ligands are shown in FIGS. 23 to 25, respectively.

As shown in FIGS. 23 to 25, the invasion of the NUGC3 cell line was induced by HB-EGF, TGF-α or AREG ligand. Specifically, when the cells were treated with 10, 20 and 50 ng/ml of HB-EGF, the cell invasion was increased by 2.3-, 3.5- and 4.8-fold, respectively, and when the cells were treated treatments with 10, 20 and 50 ng/ml of TGF-α, the cell invasion was increased by 1.7-, 1.9- and 1.9-fold, respectively. Meanwhile, when treated with 40, 200 and 500 ng/ml of AREG, cell invasion was increased by 1.2-, 1.3- and 1.5-fold, respectively.

5-2. Examination of Invasion Inhibition Effect of GC1118 Antibody in NUGC Gastric Cancer Cell Line in which Invasion was Induced by HB-EGF The cell invasion was induced by treating the NUGC3 cell line with 50 ng/ml of HB-EGF, and otherwise, the experiment was conducted by the same condition and method as Experimental Example 4-2.

As for the invasion inhibition effect, the ratio of invaded cells when treated with each antibody relative to those in the case added with HG-EGF alone was calculated as a percentage of the OD value, and the results were shown in Table 4 and FIG. 26.

TABLE 4

|  | HB-EGF (50 ng/ml) | GC1118 (1 µg/ml) | Cetuximab (1 µg/ml) | Panitumumab (1 µg/ml) | Trastuzumab (1 µg/ml) |
|---|---|---|---|---|---|
| 1-1 | 106.6 | 18.8 | 76.1 | 91.5 | 87.3 |

TABLE 4-continued

|  | HB-EGF (50 ng/ml) | GC1118 (1 µg/ml) | Cetuximab (1 µg/ml) | Panitumumab (1 µg/ml) | Trastuzumab (1 µg/ml) |
|---|---|---|---|---|---|
| 1-2 | 93.4 | 21.0 | 81.5 | 83.0 | 99.7 |
| 2-1 | 100.3 | 57.7 | 91.8 | 92.2 | 83.1 |
| 2-2 | 99.7 | 64.2 | 102.9 | 106.8 | 86.4 |
| 3-1 | 95.3 | 41.7 | 106.9 | 99.6 | 86.4 |
| 3-2 | 104.7 | 31.9 | 84.6 | 78.4 | 89.6 |
| Average (%) | 100.0 | 39.2 | 90.6 | 91.9 | 88.7 |
| Standard deviation | 5.13 | 18.84 | 12.22 | 10.42 | 5.77 |

As shown in Table 4 and FIG. 26, GC1118 showed the excellent effect of inhibiting the invasion of NUGC3 cell line induced by HB-EGF. Specifically, cetuximab, panitumumab, and trastuzumab inhibited the cell invasion by 9.4%, 8.1% and 11.3%, respectively, while GC1118 inhibited by 60.8%. That is, the cell invasion in the NUGC3 cell line induced by HB-EGF was inhibited in a GC1118-specific manner.

5-3. Examination of Invasion Inhibition Effect of GC1118 Antibody in NUGC3 Gastric Cancer Cell Line in which Invasion was Induced by TGF-α

TGF-α at a concentration of 50 ng/ml was added for treatment instead of HB-EGF, and otherwise, the inhibition of cancer cell invasion by GC1118 was examined by the same method as in Experimental Example 5-2.

As for the invasion inhibition effect, the ratio of invaded cells when treated with each antibody relative to those in the case added with TGF-α alone was calculated as a percentage of the OD value, and the results were shown in Table 5 and FIG. 27.

TABLE 5

|  | TGF-α (50 ng/ml) | GC1118 (1 µg/ml) | Cetuximab (1 µg/ml) | Panitumumab (1 µg/ml) | Trastuzumab (1 µg/ml) |
|---|---|---|---|---|---|
| 1-1 | 104.1 | 31.5 | 27.7 | 36.0 | 90.3 |
| 1-2 | 95.9 | 27.3 | 31.0 | 28.9 | 74.3 |
| 2-1 | 84.5 | 31.4 | 37.5 | 43.2 | 92.8 |
| 2-2 | 115.5 | 30.0 | 41.0 | 34.7 | 84.8 |
| 3-1 | 105.8 | 36.4 | 40.0 | 29.9 | 112.6 |
| 3-2 | 94.2 | 38.3 | 41.4 | 33.3 | 114.2 |
| Average (%) | 100.0 | 32.5 | 36.5 | 34.3 | 94.8 |
| Standard deviation | 10.77 | 4.12 | 5.74 | 5.13 | 15.72 |

As shown in Table 5 and FIG. 27, GC1118 showed the excellent effect of inhibiting the invasion of NUGC3 cell line induced by TGF-α. Specifically, GC1118 inhibited the cell invasion by 67.5%, which was similar to the level of inhibition of the control group, cetuximab (63.5%) or panitumumab (65.7%).

5-4. Examination of Invasion Inhibition Effect of GC1118 Antibody in NUGC3 Gastric Cancer Cell Line in which Invasion was Induced by AREG AREG at a concentration of 500 ng/ml was added for treatment instead of HB-EGF, and otherwise, the inhibition of cancer cell invasion by GC1118 was examined by the same method as in Experimental Example 4-4.

To examine the invasion inhibition effect, the ratio of invaded cells when treated with each antibody relative to those in the case added with AREG alone was calculated as a percentage of the OD value, and the results were shown in Table 6 and FIG. 28.

TABLE 6

|  | AREG (500 ng/ml) | GC1118 (1 µg/mi) | Cetuximab (1 µg/ml) | Panitumumab (1 µg/ml) | Trastuzumab (1 µg/ml) |
|---|---|---|---|---|---|
| 1-1 | 100.2 | 40.2 | 48.8 | 40.2 | 89.0 |
| 1-2 | 99.8 | 50.7 | 50.7 | 47.8 | 90.7 |
| 2-1 | 99.6 | 59.8 | 65.9 | 62.9 | 89.0 |
| 2-2 | 100.4 | 59.6 | 59.6 | 61.1 | 111.8 |
| 3-1 | 97.3 | 62.4 | 59.8 | 64.9 | 103.8 |
| 3-2 | 102.7 | 56.1 | 64.2 | 62.4 | 94.7 |
| Average (%) | 100.0 | 54.8 | 58.2 | 56.5 | 96.5 |
| Standard deviation | 1.74 | 8.21 | 6.98 | 10.09 | 9.35 |

As shown in Table 6 and FIG. 28, GC1118 showed the excellent effect of inhibiting the invasion of NUGC3 cell line induced by AREG. Specifically, GC1118 inhibited the cell invasion by 45.2%, which was similar to the level of inhibition of the control group, cetuximab (41.8%) or panitumumab (43.5%).

The invention claimed is:

1. A method for inhibiting metastasis of a gastric cancer in a subject in need thereof comprising administering to the subject a composition comprising an antibody or a fragment thereof that specifically binds to an EGFR, the antibody comprising:
   a) a heavy chain variable region comprising CDR1, CDR2 and CDR3 of the amino acid sequences of SEQ ID NO: 1, SEQ ID NO: 2 and SEQ ID NO: 3, respectively, a light chain variable region comprising CDR1, CDR2 and CDR3 of the amino acid sequences of SEQ ID NO: 4, SEQ ID NO: 5 and SEQ ID NO: 6, respectively, a heavy chain constant region, and a light chain constant region; or
   b) a heavy chain variable region comprising CDR1, CDR2 and CDR3 of the amino acid sequences of SEQ ID NO: 1, SEQ ID NO: 2 and SEQ ID NO: 3, respectively, a light chain variable region comprising CDR1, CDR2 and CDR3 of the amino acid sequences of SEQ ID NO: 9, SEQ ID NO: 5 and SEQ ID NO: 6, respectively, a heavy chain constant region, and a light chain constant region.

2. The method of claim 1, wherein the antibody or a fragment thereof comprises:
   a) a heavy chain variable region of the amino acid sequence of SEQ ID NO: 7, a light chain variable region of the amino acid sequence of SEQ ID NO: 8, a heavy chain constant region, and a light chain constant region; or
   b) a heavy chain variable region of the amino acid sequence of SEQ ID NO: 7, a light chain variable region of the amino acid sequence of SEQ ID NO: 10, a heavy chain constant region, and a light chain constant region.

3. The method of claim 1, wherein the metastasis is induced or promoted by an EGFR ligand.

4. The method of claim 3, wherein the EGFR ligand is selected from the group consisting of heparin binding-EGF-like growth factor (HB-EGF), transforming growth factor-α (TGF-α), amphiregulin (AREG), and a combination thereof.

5. The method of claim 1, wherein the composition further comprises one or more selected from the group consisting of a pharmaceutically acceptable carrier, an excipient, a lubricant, a humectant, a sweetener, a flavoring agent, a preservative and a mixture thereof.

* * * * *